(12) United States Patent
Wojcik et al.

(10) Patent No.: US 10,638,986 B2
(45) Date of Patent: May 5, 2020

(54) MODULAR SINGLE SHOT DIGITAL RADIOGRAPHY FOR LONG-LENGTH IMAGING

(71) Applicant: CARESTREAM HEALTH, INC., Rochester, NY (US)

(72) Inventors: Timothy J. Wojcik, Rochester, NY (US); Jacob M. Fornof, Fairport, NY (US); Craig F. Hofmann, Fairport, NY (US); Martin S. Pesce, Quarkertown, PA (US); Mark E. Shafer, Fairport, NY (US); Jeffery R. Hawver, Marion, NY (US); Steven R. Lippold, Bergen, NY (US); Todd D. Bogumil, Rochester, NY (US)

( * ) Notice: Subject to any disclaimer, the term of this patent is extended or adjusted under 35 U.S.C. 154(b) by 0 days.

(21) Appl. No.: 16/361,280

(22) Filed: Mar. 22, 2019

(65) Prior Publication Data

US 2019/0216415 A1 Jul. 18, 2019

Related U.S. Application Data

(63) Continuation-in-part of application No. 15/815,948, filed on Nov. 17, 2017, now Pat. No. 10,251,614, which is a continuation of application No. 14/942,081, filed on Nov. 16, 2015, now Pat. No. 9,820,703.

(60) Provisional application No. 62/769,840, filed on Nov. 20, 2018, provisional application No. 62/647,045, (Continued)

(51) Int. Cl.
*A61B 6/04* (2006.01)
*G01N 23/04* (2018.01)
*A61B 6/00* (2006.01)

(52) U.S. Cl.
CPC .......... *A61B 6/4233* (2013.01); *A61B 6/4283* (2013.01); *A61B 6/4411* (2013.01); *A61B 6/4405* (2013.01); *A61B 6/56* (2013.01)

(58) Field of Classification Search
CPC ................ G01N 23/04; G01N 23/046; G01N 2223/301; G01N 2223/1016; A61B 6/4405; A61B 6/4208; A61B 6/4266; A61B 6/4452; A61B 6/4411
See application file for complete search history.

(56) References Cited

U.S. PATENT DOCUMENTS

| 5,440,130 A | 8/1995 | Cox et al. |
| 5,986,279 A | 11/1999 | Dewaele |
| 6,273,606 B1 | 8/2001 | Dewaele et al. |

(Continued)

FOREIGN PATENT DOCUMENTS

| CN | 105832351 A | 8/2016 |
| EP | 0 919 856 B1 | 12/1997 |

(Continued)

*Primary Examiner* — Don K Wong

(57) ABSTRACT

A digital radiographic detector system includes a number of DR detectors enclosed by a housing. A base section with wheels has attached thereto a vertical column with a height adjustable horizontal arm extending therefrom. The housing with DR detectors therein is attached to a distal end of the horizontal arm. The housing comprises a major surface made from a radiolucent material to allow the detectors to capture radiographic images via x-rays transmitted through the major surface of the housing. The housing is configured to support the plurality of DR detectors therewithin.

20 Claims, 23 Drawing Sheets

Related U.S. Application Data filed on Mar. 23, 2018, provisional application No. 62/080,454, filed on Nov. 17, 2014.

(56) References Cited

U.S. PATENT DOCUMENTS

| | | |
|---|---|---|
| 6,614,032 B2 | 9/2003 | Wendlandt |
| 6,807,250 B2 | 10/2004 | Wang et al. |
| 7,127,090 B2 | 10/2006 | Kreang-Arekul et al. |
| 7,247,858 B2 | 7/2007 | De Keyser |
| 7,498,583 B2 | 3/2009 | Shoji et al. |
| 8,351,568 B2 | 1/2013 | Minnigh et al. |
| 8,600,193 B2 | 12/2013 | Kalayeh |
| 8,606,052 B2 | 12/2013 | Mercur'ev |
| 8,748,834 B2 | 6/2014 | Enomoto |
| 8,767,913 B2 | 7/2014 | Okuno |
| 9,239,392 B2 | 1/2016 | Gemma et al. |
| 9,532,764 B2 | 1/2017 | Graumann |
| 10,058,294 B2 | 8/2018 | Tagawa |
| 2009/0238341 A1 | 9/2009 | Kawamura et al. |
| 2011/0198503 A1 | 8/2011 | Koren et al. |
| 2011/0233415 A1 | 9/2011 | Nakatsugawa et al. |
| 2013/0004085 A1 | 1/2013 | Bai et al. |
| 2013/0114790 A1* | 5/2013 | Fabrizio .......... A61B 6/02 378/62 |
| 2015/0131785 A1 | 5/2015 | Topfer et al. |
| 2015/0247936 A1 | 9/2015 | Gemma et al. |
| 2016/0074001 A1 | 3/2016 | Matsushita et al. |
| 2016/0287202 A1 | 10/2016 | Miyachi |
| 2016/0302755 A1 | 10/2016 | Takagi et al. |
| 2018/0055465 A1 | 3/2018 | Nakayama et al. |

FOREIGN PATENT DOCUMENTS

| | | |
|---|---|---|
| EP | 2082687 B | 4/2015 |
| JP | 5644195 B2 | 11/2014 |
| JP | 2015-218778 A | 12/2015 |
| JP | 2016-202251 A | 12/2016 |
| JP | 2017-077405 A | 4/2017 |

* cited by examiner

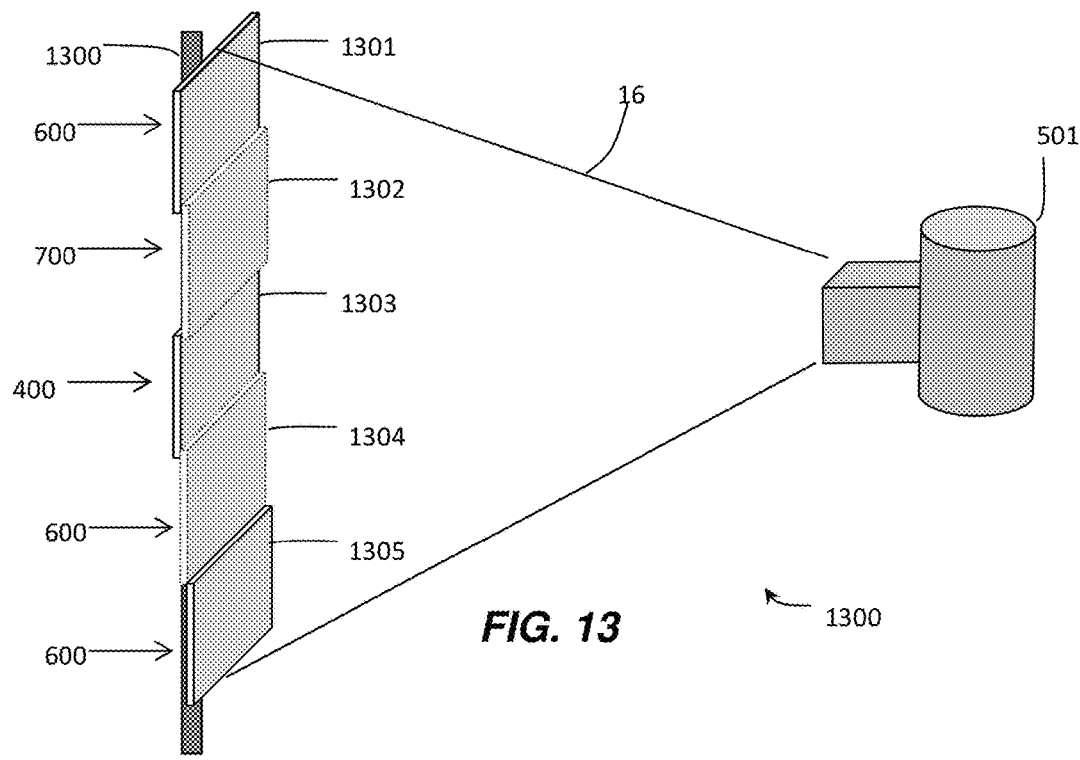
FIG. 13
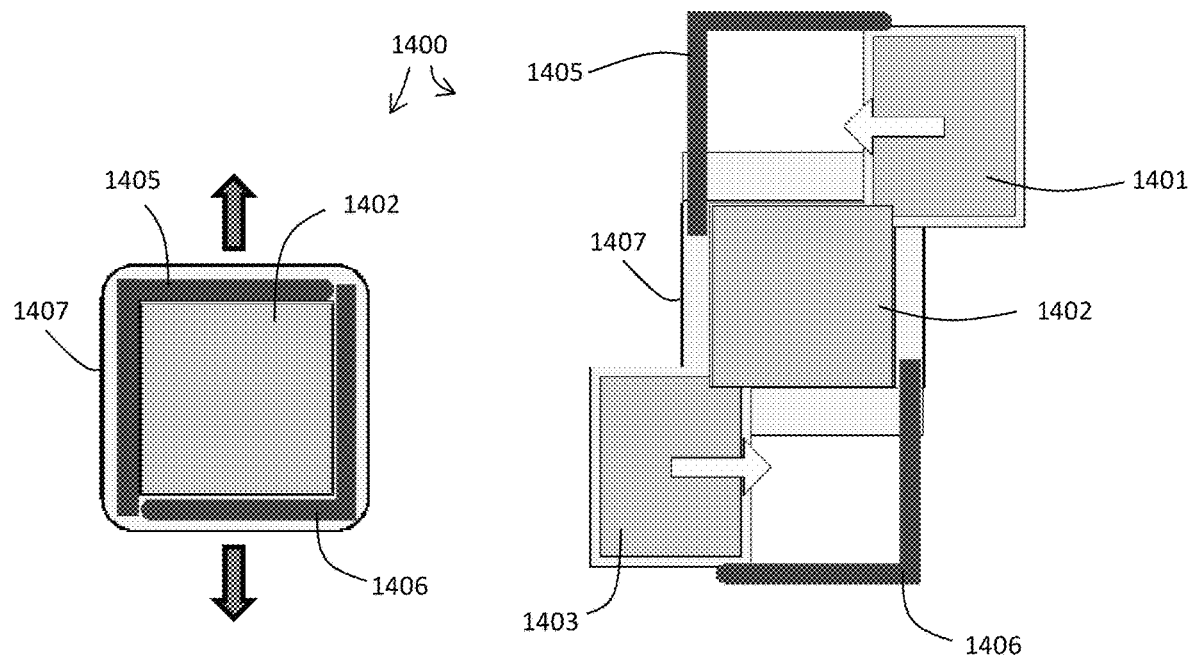
FIG. 14A
FIG. 14B

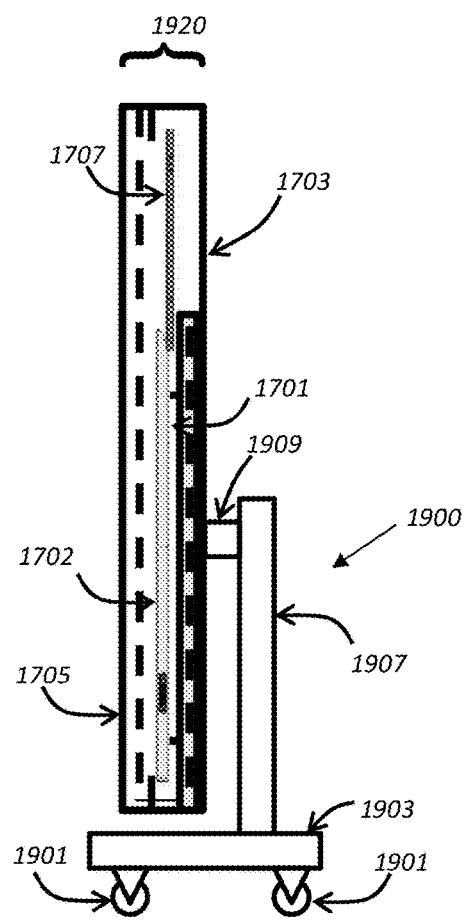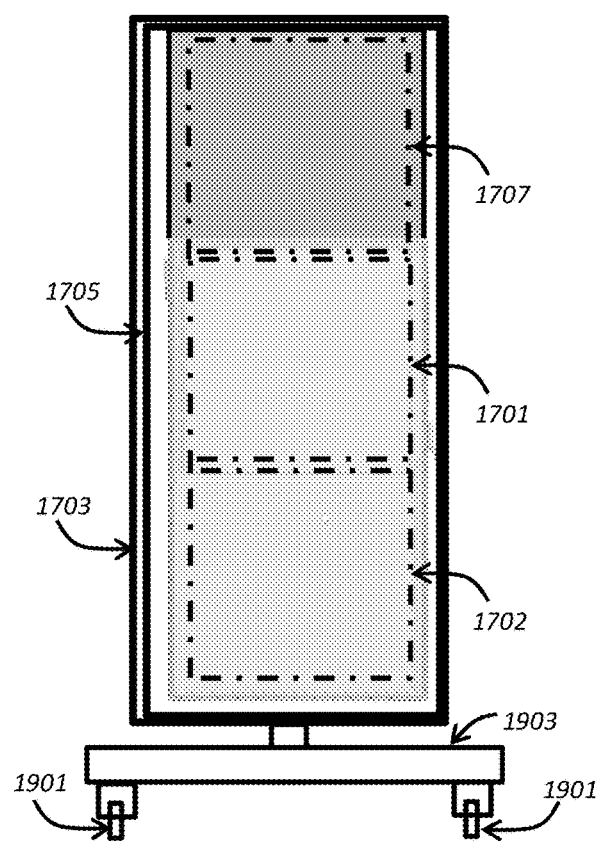
FIG. 21A     FIG. 21B

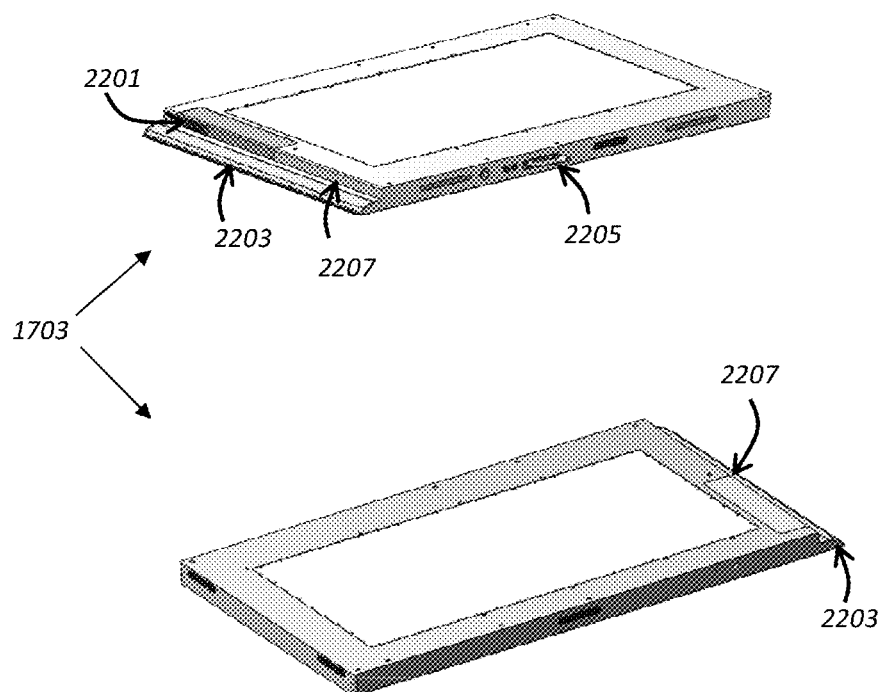
FIG. 22A
FIG. 22B
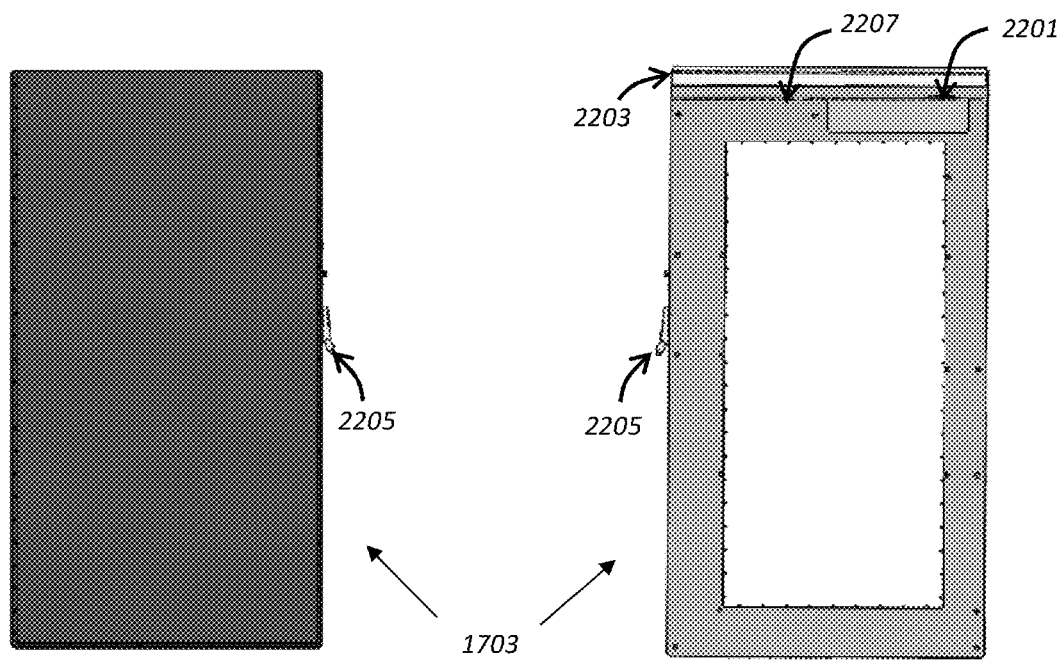
FIG. 22C
FIG. 22D

MODULAR SINGLE SHOT DIGITAL RADIOGRAPHY FOR LONG-LENGTH IMAGING

CROSS REFERENCE TO RELATED APPLICATIONS

This application is a continuation-in-part of, and claims priority to, U.S. patent application Ser. No. 15/815,948, filed Nov. 17, 2017, in the name of Wojcik et al., and entitled TILED DIGITAL RADIOGRAPHY DETECTORS FOR LONG-LENGTH IMAGING, which is a continuation of U.S. patent application Ser. No. 14/942,081, filed Nov. 16, 2015, in the name of Wojcik et al., and entitled TILED DIGITAL RADIOGRAPHY DETECTORS FOR LONG-LENGTH IMAGING, which claims priority to U.S. Patent Application Ser. No. 62/080,454, filed Nov. 17, 2014, in the name of Wojcik et al., and entitled TILED DIGITAL RADIOGRAPHY DETECTORS FOR LONG-LENGTH IMAGING; this application also claims priority to U.S. Patent Application Ser. No. 62/769,840, filed Nov. 20, 2018, in the name of Wojcik et al., and entitled SINGLE SHOT DIGITAL RADIOGRAPHY FOR LONG-LENGTH IMAGING; this application also claims priority to U.S. Patent Application Ser. No. 62/647,045, filed Mar. 23, 2018, in the name of Wojcik et al., and entitled MODULAR SINGLE SHOT DIGITAL RADIOGRAPHY FOR LONG-LENGTH IMAGING.

BACKGROUND OF THE INVENTION

The subject matter disclosed herein relates to digital radiography (DR) imaging, in particular, to long-length imaging that requires multiple DR detectors.

Special cassettes and films of extended length are sometimes used when imaging a long segment of a subject, such as a human body, with an analog screen-film technique. An x-ray source and the cassette are both centered to the subject to be examined and an x-ray collimator is adjusted to cover the imaging area, whereby a single x-ray exposure is performed. Flat-panel DR detectors are usually limited to 43 cm in length. For long-length imaging applications this would require separate exposures to be taken at different regions of the subject. In order to create a large, single composite image for diagnosis, the individually captured images of the subject need to be stitched together using digital computer-implemented reconstruction techniques.

Two primary approaches are available to acquire long-length imaging exams with flat-panel detectors. In both methods, the detector moves from one imaging position to the next behind the subject. In one known embodiment, the x-ray energy source moves (rotates or tilts) in order to track and expose the detector. In this x-ray source tilting method, the central x-ray pointing direction varies from one exposure position to the next to deliver the x-rays to the detector. In another known embodiment, the x-ray source focal spot position is not stationary, but translates synchronously with the DR detector parallel to the detector's axis of travel.

There are advantages to both embodiments. For example, the tilt method is free of parallax artifacts inherent in the x-ray source translation method. Because of parallax distortion, the geometric integrity of the subject's features in the stitched image may be degraded, particularly in the stitch overlap regions. Automatic image stitching can be achieved with high geometric accuracy such as provided by the Carestream DR DirectView Long-Length Imaging System. A high-precision hardware encoder reports the exact detector travel distance between exposures. In a direction transverse to the detector motion axis, software automatically analyzes the subject's features in the overlap regions to find the best alignment between any two adjacent images. The total stitch error has been demonstrated to be small under stringent exposure conditions.

Automatic exposure control can be used during the long-length imaging exams in order to apply just the right amount of exposure to each region of the subject for image quality. Software may also automatically adjust exposure discrepancies and compensate for the latitude differences, therefore providing optimized image presentation for each image. The image-processing reconstruction algorithm stitches together the individually optimized, display-presentation-ready images to create a smooth and seamless composite single image for diagnosis. The seam line between any two images may be blended without any visible artifacts during this digital process. Such imaging software should be able to adjust and fine-tune stitch positions to compensate for movement of the subject during the exam to avoid exposure retakes. In all of the examples just described, it would be advantageous if multiple DR detectors could be used to simultaneously capture a composite radiographic image of a subject in a single exposure.

The discussion above is merely provided for general background information and is not intended to be used as an aid in determining the scope of the claimed subject matter.

BRIEF DESCRIPTION OF THE INVENTION

A long length imaging system having a host processor, an x-ray source, and a plurality of radiographic detectors is configured to simultaneously capture a radiographic image of a portion of a subject exposed by the x-ray source, and to transmit the partial images to the host processor whereby the partial images are combined into a long length image. An advantage that may be realized in the practice of some disclosed embodiments of multiple DR detector systems is that the images are simultaneously exposed and potential movement of the subject during an imaging exam is eliminated, which results in improved long-length image reconstruction and reduced radiation exposure for a subject.

It is recognized that a significant portion of long length imaging requires an active imaging area of at least about 17"×33" and preferably expandable to about a 17"×49" active imaging area. The low attenuation DR detector edge disclosed herein may be used for such embodiments, and additional configurations described herein are optimized for these sizes of active imaging areas.

Advantages that may be realized in the practice of some disclosed embodiments of the LLI DR detector embodiments disclosed herein include reducing seam artifacts within a LLI area by using a monolithic sensor glass or two tiled sensor panels in a single housing; retaining connection of DR detector module to a positioning device obviating the need for a user to lift and position components; utilizing a portable positioning device to enable erect, supine, and cross table imaging of a patient in an x-ray exam room, or in bedside locations such as the operating room, emergency room or intensive care unit; and the arrangement can be expanded by utilizing an additional portable DR detector.

In one embodiment, a digital radiographic detector system includes a number of DR detectors enclosed by a housing. A base section with wheels has attached thereto a vertical column with a height adjustable horizontal arm extending therefrom. The housing with DR detectors therein is attached to a distal end of the horizontal arm. The housing comprises a major surface made from a radiolucent material to allow the detectors to capture radiographic images via x-rays transmitted through the major surface of the housing. The housing is configured to support the plurality of DR detectors therewithin.

In another embodiment, a digital radiographic detector system includes a base affixed to a floor and a vertical column attached to the base. A movable support is attached to the vertical column and is movable vertically along the vertical column. A housing is attached to the support and has secured therein a plurality of DR detectors each facing a major surface of the housing which is made from a radiolucent material.

In another embodiment, a digital radiographic detector system includes a vertical hanger having a plurality of first detent portions (slots) arranged vertically in relation to one another. The vertical hanger is attached to a vertical surface such as a wall. A manually movable support is attached to the vertical hanger and is configured to move vertically along the vertical hanger. The movable support has a second detent portion to lockably engage any one of the first detent portions. A housing is attached to the movable support, the housing encloses and supports therewithin a plurality of DR detectors each facing a major surface of the housing which is made from a radiolucent material, which major surface faces away from the vertical surface.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. For example, the summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation. In the drawings, like numerals are used to indicate like parts throughout the various views. Thus, for further understanding of the invention, reference can be made to the following detailed description, read in connection with the drawings in which:

FIG. 13 is a perspective view of an exemplary imaging system implementing an arrangement of DR detectors according to one embodiment;

FIGS. 14A-B are front views of an exemplary bucky apparatus according to one embodiment;

FIGS. 21A-B illustrates side and front views, respectively, of another exemplary DR LLI mobile system;

FIGS. 22A-D illustrate various views of an exemplary DR LLI assembly;

DETAILED DESCRIPTION OF THE INVENTION

Figure 1:
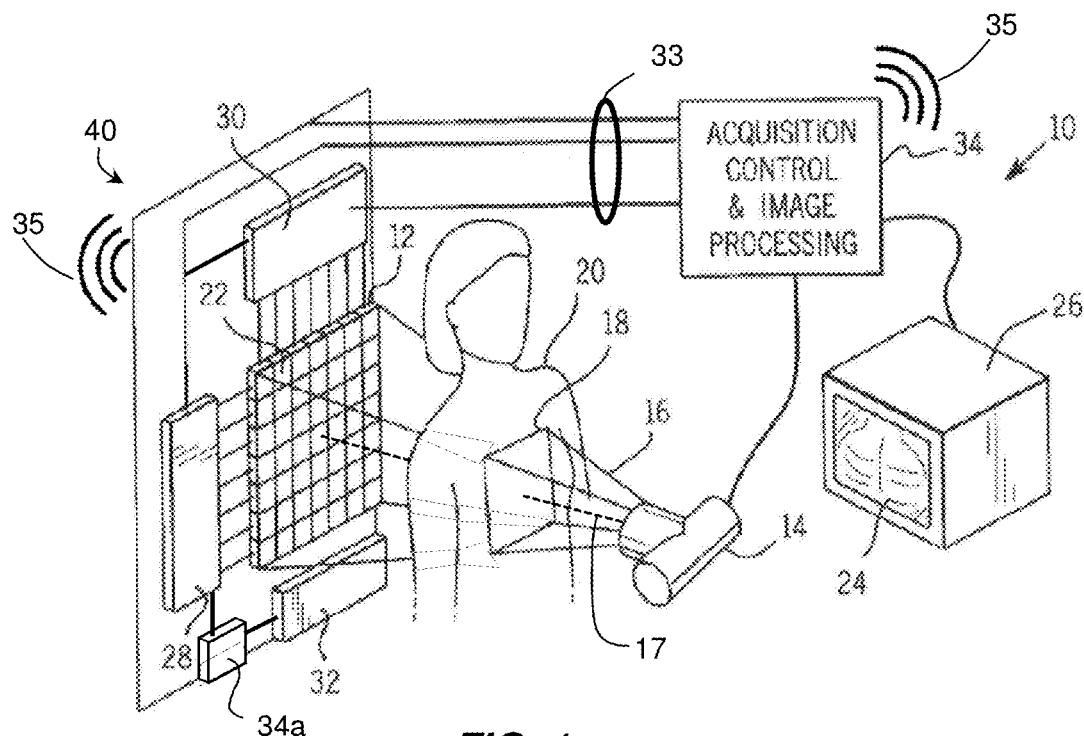
FIG. 1 is a diagram of an exemplary radiographic imaging system.

FIG. 1 is a perspective view of a digital radiographic (DR) imaging system 10 that may include a generally curved or planar DR detector 40 (shown in a planar embodiment and without a housing for clarity of description), an x-ray source 14 configured to generate radiographic energy (x-ray radiation), and a digital monitor, or electronic display, 26 configured to display images captured by the DR detector 40, according to one embodiment. The DR detector 40 may include a two dimensional array 12 of detector cells 22 (photosensors), arranged in electronically addressable rows and columns. The DR detector 40 may be positioned to receive x-rays 16 passing through a subject 20 during a radiographic energy exposure, or radiographic energy pulse, emitted by the x-ray source 14. As shown in FIG. 1, the radiographic imaging system 10 may use an x-ray source 14 that emits collimated x-rays 16, e.g. an x-ray beam, selectively aimed at and passing through a preselected region 18 of the subject 20. The x-ray beam 16 may be attenuated by varying degrees along its plurality of rays according to the internal structure of the subject 20, which attenuated rays are detected by the array 12 of photosensitive detector cells 22. The curved or planar DR detector 40 is positioned, as much as possible, in a perpendicular relation to a substantially central ray 17 of the plurality of rays 16 emitted by the x-ray source 14. In a curved array embodiment, the source 14 may be centrally positioned such that a larger percentage, or all, of the photosensitive detector cells are positioned perpendicular to incoming x-rays from the centrally positioned source 14. The array 12 of individual photosensitive cells (pixels) 22 may be electronically addressed (scanned) by their position according to column and row. As used herein, the terms "column" and "row" refer to the vertical and horizontal arrangement of the photosensor cells 22 and, for clarity of description, it will be assumed that the rows extend horizontally and the columns extend vertically. However, the orientation of the columns and rows is arbitrary and does not limit the scope of any embodiments disclosed herein. Furthermore, the term "subject" may be illustrated as a human patient in the description of FIG. 1, however, a subject of a DR imaging system, as the term is used herein, may be a human, an animal, an inanimate object, or a portion thereof.

In one exemplary embodiment, the rows of photosensitive cells 22 may be scanned one or more at a time by electronic scanning circuit 28 so that the exposure data from the array 12 may be transmitted to electronic read-out circuit 30. Each photosensitive cell 22 may independently store a charge proportional to an intensity, or energy level, of the attenuated radiographic radiation, or x-rays, received and absorbed in the cell. Thus, each photosensitive cell, when read-out, provides information defining a pixel of a radiographic image 24, e.g. a brightness level or an amount of energy absorbed by the pixel, that may be digitally decoded by image processing electronics 34 and transmitted to be displayed by the digital monitor 26 for viewing by a user. An electronic bias circuit 32 is electrically connected to the two-dimensional detector array 12 to provide a bias voltage to each of the photosensitive cells 22.

Each of the bias circuit 32, the scanning circuit 28, and the read-out circuit 30, may communicate with an acquisition control and image processing unit 34 over a connected cable 33 (wired), or the DR detector 40 and the acquisition control and image processing unit 34 may be equipped with a wireless transmitter and receiver to transmit radiographic image data wirelessly 35 to the acquisition control and image processing unit 34. The acquisition control and image processing unit 34 may include a processor and electronic memory (not shown) to control operations of the DR detector 40 as described herein, including control of circuits 28, 30, and 32, for example, by use of programmed instructions, and to store and process image data. The acquisition control and image processing unit 34 may also be used to control activation of the x-ray source 14 during a radiographic exposure, controlling an x-ray tube electric current magnitude, and thus the fluence of x-rays in x-ray beam 16, and/or the x-ray tube voltage, and thus the energy level of the x-rays in x-ray beam 16. The acquisition control and image processing unit 34 may be referred to herein as a host system or a central processing system. Typically, such a host system may be configured to control and manage operations of the radiographic imaging system 10 automatically or by providing an operator with various input devices to control exposure operations.

A portion or all of the acquisition control and image processing unit 34 functions may reside in the detector 40 in an on-board processing system 34a which may include a processor and electronic memory to control operations of the DR detector 40 as described herein, including control of circuits 28, 30, and 32, by use of programmed instructions, and to store and process image data similar to the functions of standalone acquisition control and image processing system 34. The on-board processing system 34a may include sufficient electronic memory to store several raw and/or fully processed (e.g., gain, offset, and defect corrected) DR images. The image processing system may perform image acquisition and image disposition functions as described herein. The image processing system 34a may control image transmission and image processing and image correction on board the detector 40 based on instructions or other commands transmitted from the acquisition control and image processing unit 34, and transmit corrected digital image data therefrom. Alternatively, acquisition control and image processing unit 34 may receive raw image data from the detector 40 and process the image data and store it, or it may store raw unprocessed image data in local memory, or in remotely accessible memory.

With regard to a direct detection embodiment of DR detector 40, the photosensitive cells 22 may each include a sensing element sensitive to x-rays, i.e. it absorbs x-rays and generates an amount of charge carriers in proportion to a magnitude of the absorbed x-ray energy. A switching element may be configured to be selectively activated to read out the charge level of a corresponding x-ray sensing element. With regard to an indirect detection embodiment of DR detector 40, photosensitive cells 22 may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, may be disposed over the light sensitive sensing elements to convert incident x-ray radiographic energy to visible light energy. Thus, in the embodiments disclosed herein, it should be noted that the DR detector 40 (or DR detector 300 in FIG. 3 or DR detector 400 in FIG. 4) may include an indirect or direct type of DR detector.

Examples of sensing elements used in sensing array 12 include various types of photoelectric conversion devices (e.g., photosensors) such as photodiodes (P-N or PIN diodes), photo-capacitors (MIS), photo-transistors or photoconductors. Examples of switching elements used for signal read-out include a-Si TFTs, oxide TFTs, MOS transistors, bipolar transistors and other p-n junction components.

Figure 2:
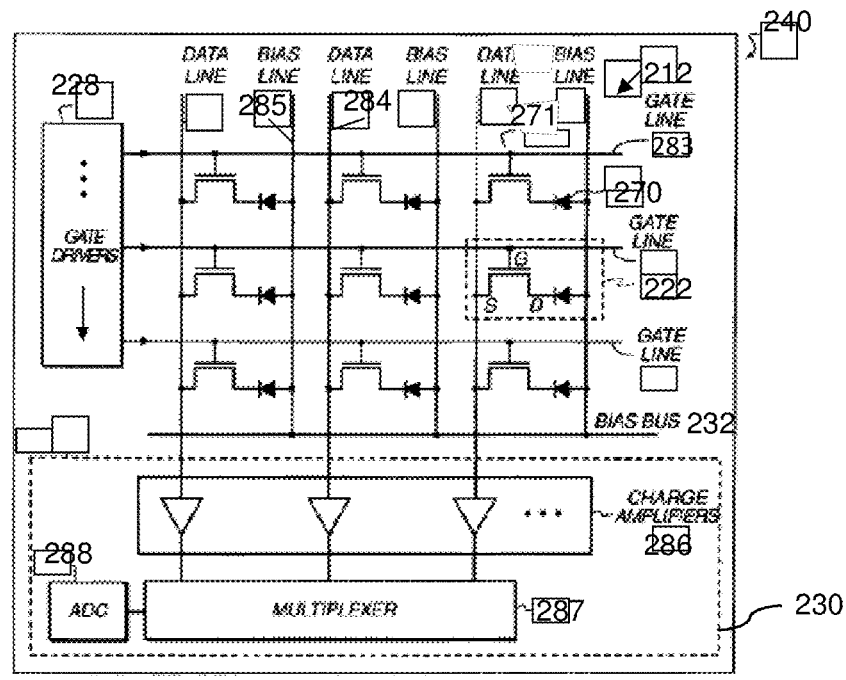
FIG. 2 is a schematic diagram of an exemplary imaging array for a radiographic detector.

FIG. 2 is a schematic diagram 240 of a portion of a two-dimensional array 12 for a DR detector 40. The array of photosensor cells 212, whose operation may be consistent with the photosensor array 12 described above, may include a number of hydrogenated amorphous silicon (a-Si:H) n-i-p photodiodes 270 and thin film transistors (TFTs) 271 formed as field effect transistors (FETs) each having gate (G), source (S), and drain (D) terminals. In embodiments of DR detector 40 disclosed herein, such as a multilayer DR detector (400 of FIG. 4), the two-dimensional array of photosensor cells 12 may be formed in a device layer that abuts adjacent layers of the DR detector structure, which adjacent layers may include a rigid glass layer or a flexible polyimide layer or a layer comprising carbon fiber without any adjacent rigid layers. A plurality of gate driver circuits 228 may be electrically connected to a plurality of gate lines 283 which control a voltage applied to the gates of TFTs 271, a plurality of readout circuits 230 may be electrically connected to data lines 284, and a plurality of bias lines 285 may be electrically connected to a bias line bus or a variable bias reference voltage line 232 which controls a voltage applied to the photodiodes 270. Charge amplifiers 286 may be electrically connected to the data lines 284 to receive signals therefrom. Outputs from the charge amplifiers 286 may be electrically connected to a multiplexer 287, such as an analog multiplexer, then to an analog-to-digital converter (ADC) 288, or they may be directly connected to the ADC, to stream out the digital radiographic image data at desired rates. In one embodiment, the schematic diagram of FIG. 2 may represent a portion of a DR detector 40 such as an a-Si:H based indirect flat panel, curved panel, or flexible panel imager.

Incident x-rays, or x-ray photons, 16 are converted to optical photons, or light rays, by a scintillator, which light rays are subsequently converted to electron-hole pairs, or charges, upon impacting the a-Si:H n-i-p photodiodes 270. In one embodiment, an exemplary detector cell 222, which may be equivalently referred to herein as a pixel, may include a photodiode 270 having its anode electrically connected to a bias line 285 and its cathode electrically connected to the drain (D) of TFT 271. The bias reference voltage line 232 can control a bias voltage of the photodiodes 270 at each of the detector cells 222. The charge capacity of each of the photodiodes 270 is a function of its bias voltage and its capacitance. In general, a reverse bias voltage, e.g. a negative voltage, may be applied to the bias lines 285 to create an electric field (and hence a depletion region) across the pn junction of each of the photodiodes 270 to enhance its collection efficiency for the charges generated by incident light rays. The image signal represented by the array of photosensor cells 212 may be integrated by the photodiodes while their associated TFTs 271 are held in a non-conducting (off) state, for example, by maintaining the gate lines 283 at a negative voltage via the gate driver circuits 228. The photosensor cell array 212 may be read out by sequentially switching rows of the TFTs 271 to a conducting (on) state by means of the gate driver circuits 228. When a row of the pixels 22 is switched to a conducting state, for example by applying a positive voltage to the corresponding gate line 283, collected charge from the photodiode in those pixels may be transferred along data lines 284 and integrated by the external charge amplifier circuits 286. The row may then be switched back to a non-conducting state, and the process is repeated for each row until the entire array of photosensor cells 212 has been read out. The integrated signal outputs are transferred from the external charge amplifiers 286 to an analog-to-digital converter (ADC) 288 using a parallel-to-serial converter, such as multiplexer 287, which together comprise read-out circuit 230.

This digital image information may be subsequently processed by image processing system 34 to yield a digital image which may then be digitally stored and immediately displayed on monitor 26, or it may be displayed at a later time by accessing the digital electronic memory containing the stored image. The flat panel DR detector 40 having an imaging array as described with reference to FIG. 2 is capable of both single-shot (e.g., static, radiographic) and continuous (e.g., fluoroscopic) image acquisition.

Figure 3:
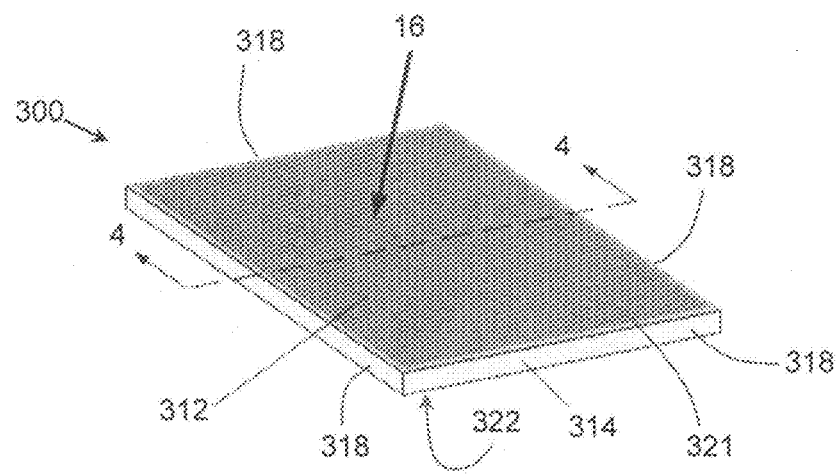
FIG. 3 shows a perspective view of an exemplary portable wireless DR detector.

FIG. 3 shows a perspective view of an exemplary prior art generally rectangular, planar, portable wireless DR detector 300 according to an embodiment of DR detector 40 disclosed herein. The DR detector 300 may include a flexible substrate to allow the DR detector to capture radiographic images in a curved orientation. The flexible substrate may be fabricated in a permanent curved orientation, or it may remain flexible throughout its life to provide an adjustable curvature in two or three dimensions, as desired. The DR detector 300 may include a similarly flexible housing portion 314 that surrounds a multilayer structure comprising a flexible photosensor array portion 22 of the DR detector 300. The housing portion 314 of the DR detector 300 may include a continuous, rigid or flexible, x-ray opaque material or, as used synonymously herein a radio-opaque material, surrounding an interior volume of the DR detector 300. The housing portion 314 may include four flexible edges 318, extending between the top side 321 and the bottom side 322, and arranged substantially orthogonally in relation to the top and bottom sides 321, 322. The bottom side 322 may be continuous with the four edges and disposed opposite the top side 321 of the DR detector 300. The top side 321 comprises a top cover 312 attached to the housing portion 314 which, together with the housing portion 314, substantially encloses the multilayer structure in the interior volume of the DR detector 300. The top cover 312 may be attached to the housing 314 to form a seal therebetween, and be made of a material that passes x-rays 16 without significant attenuation thereof, i.e., an x-ray transmissive material or, as used synonymously herein, a radiolucent material, such as a carbon fiber plastic, polymeric, or other plastic based material.

Figure 4:
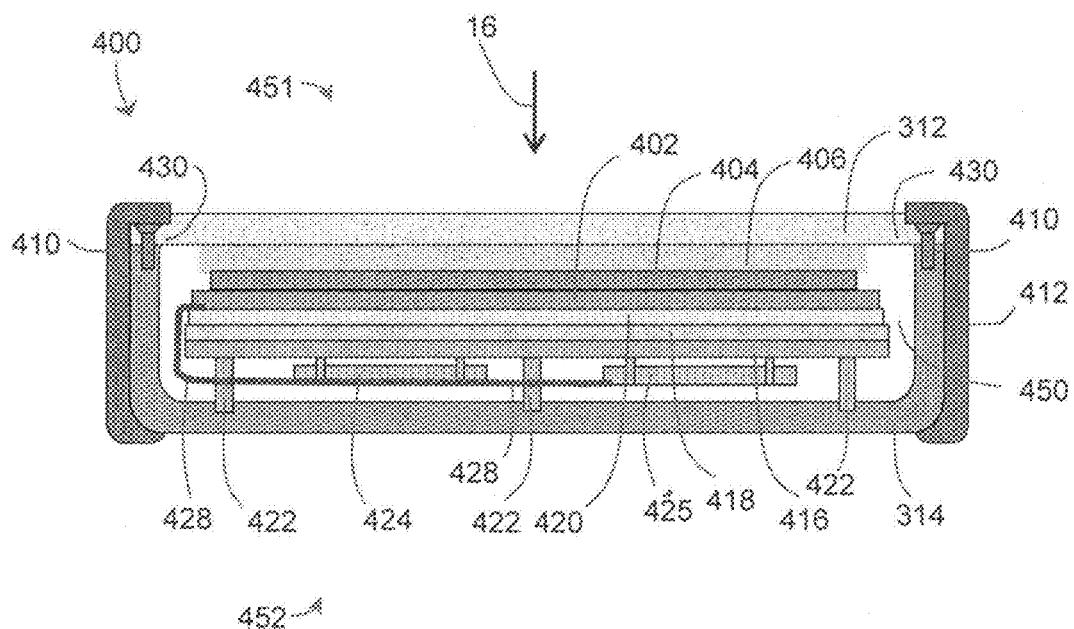
FIG. 4 is a cross-section of a portion of the exemplary portable wireless DR detector of FIG. 3 along section line 4-4.

With reference to FIG. 4, there is illustrated in schematic form an exemplary cross-section view along section 4-4 of the exemplary embodiment of the DR detector 300 (FIG. 3). For spatial reference purposes, one major surface of the DR detector 400 may be referred to as the top side 451 and a second major surface may be referred to as the bottom side 452, as used herein. The multilayer structure may be disposed within the interior volume 450 enclosed by the housing 314 and top cover 312 and may include a flexible curved or planar scintillator layer 404 over a curved or planar the two-dimensional imaging sensor array 12 shown schematically as the device layer 402. The scintillator layer 404 may be directly under (e.g., directly connected to) the substantially planar top cover 312, and the imaging array 402 may be directly under the scintillator 404. Alternatively, a flexible layer 406 may be positioned between the scintillator layer 404 and the top cover 312 as part of the multilayer structure to allow adjustable curvature of the multilayer structure and/or to provide shock absorption. The flexible layer 406 may be selected to provide an amount of flexible support for both the top cover 312 and the scintillator 404, and may comprise a foam rubber type of material. The layers just described comprising the multilayer structure each may generally be formed in a rectangular shape and defined by edges arranged orthogonally and disposed in parallel with an interior side of the edges 318 of the housing 314, as described in reference to FIG. 3.

A substrate layer 420 may be disposed under the imaging array 402, such as a rigid glass layer, in one embodiment, or a flexible substrate comprising polyimide or carbon fiber upon which the array of photosensors 402 may be formed to allow adjustable curvature of the array, and may comprise another layer of the multilayer structure. Under the substrate layer 420 a radio-opaque shield layer 418 may be used as an x-ray blocking layer to help prevent scattering of x-rays passing through the substrate layer 420 as well as to block x-rays reflected from other surfaces in the interior volume 450. Readout electronics, including the scanning circuit 28, the read-out circuit 30, the bias circuit 32, and processing system 34a (all of FIG. 1) may be formed adjacent the imaging array 402 or, as shown, may be disposed below frame support member 416 in the form of integrated circuits (ICs) electrically connected to printed circuit boards 424, 425. The imaging array 402 may be electrically connected to the readout electronics 424 (ICs) over a flexible connector 428 which may comprise a plurality of flexible, sealed conductors known as chip-on-film (COF) connectors.

X-ray flux may pass through the radiolucent top panel cover 312, in the direction represented by an exemplary x-ray beam 16, and impinge upon scintillator 404 where stimulation by the high-energy x-rays 16, or photons, causes the scintillator 404 to emit lower energy photons as visible light rays which are then received in the photosensors of imaging array 402. The frame support member 416 may connect the multilayer structure to the housing 314 and may further operate as a shock absorber by disposing elastic pads (not shown) between the frame support beams 422 and the housing 314. Fasteners 410 may be used to attach the top cover 312 to the housing 314 and create a seal therebetween in the region 430 where they come into contact. In one embodiment, an external bumper 412 may be attached along the edges 318 of the DR detector 400 to provide additional shock-absorption.

Figure 5:
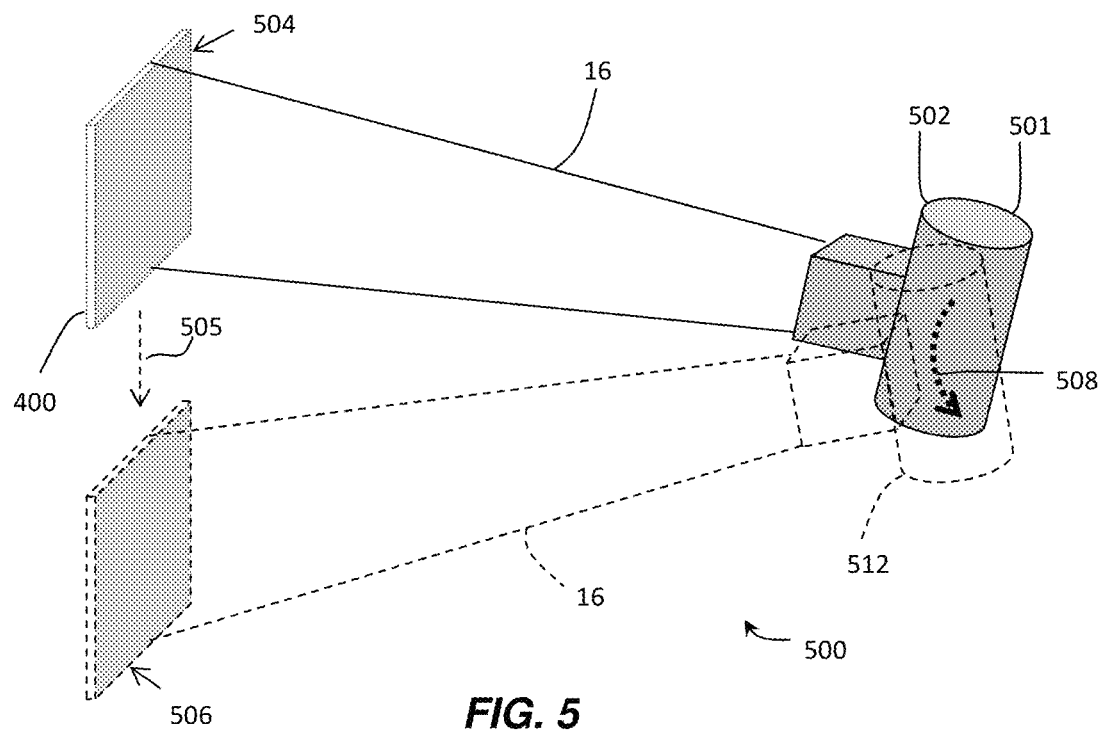
FIG. 5 is a diagram of an exemplary radiographic imaging system illustrating positioning of the radiographic energy source and the DR detector.

FIG. 5 illustrates operation of an embodiment of an imaging system 500 which may be used for long-length radiographic imaging of a stationary subject (not shown) positioned between an x-ray source 501 and DR detector 400. The x-ray radiation source 501 in the first position 502 is aimed at DR detector 400 in position 504 to capture a first radiographic image of the subject. In the embodiment shown in FIG. 5, the x-ray radiation source may be tilted in the direction indicated by arrow 508 to a second position 512 and aimed at DR detector 400 in position 506 to capture a second image of the stationary subject, wherein the first and second images each include an image of a different region of the same subject. In the embodiment of FIG. 5, a single DR detector 400 may be moved in the direction indicated by arrow 505 from the first position 504 to the second position 506 to capture the two images of the subject as just described. In another embodiment, two or more separate DR detectors 400 may be used, one in each of positions 504 and 506, and in positions in between, wherein each DR detector 400 is exposed to one radiographic pulse from the x-ray source 501 firing energy pulses at positions 502 and 512, and in corresponding positions in between. In another embodiment, the DR detector 400 may be moved to one or more intermediate positions between positions 504 and 506, with corresponding intermediate tilt positions of the x-ray source 501 between positions 502 and 512 to capture one or more additional radiographic images. In another embodiment, the x-ray source may be attached to a support at a fixed angle such that the x-ray source 501 is not tiltable, rather, the support is configured to move vertically and is used to translate the x-ray source 501 to a position corresponding to the DR detector positions 504 and 506, or to intermediate positions of the DR detector 400 as just described. Thus, it should be understood that embodiments of imaging system 500 may include various combinations of one or more DR detectors 400, which may be fixed or moveable, together with an x-ray source 501 that may be tiltable and/or vertically translatable. In one embodiment, the one or more positions of DR detector 400 may overlap, resulting in a plurality of captured radiographic images that may be stitched together into one long-length digital image of the subject using known computer-implemented image reconstruction processing techniques.

Figure 6:
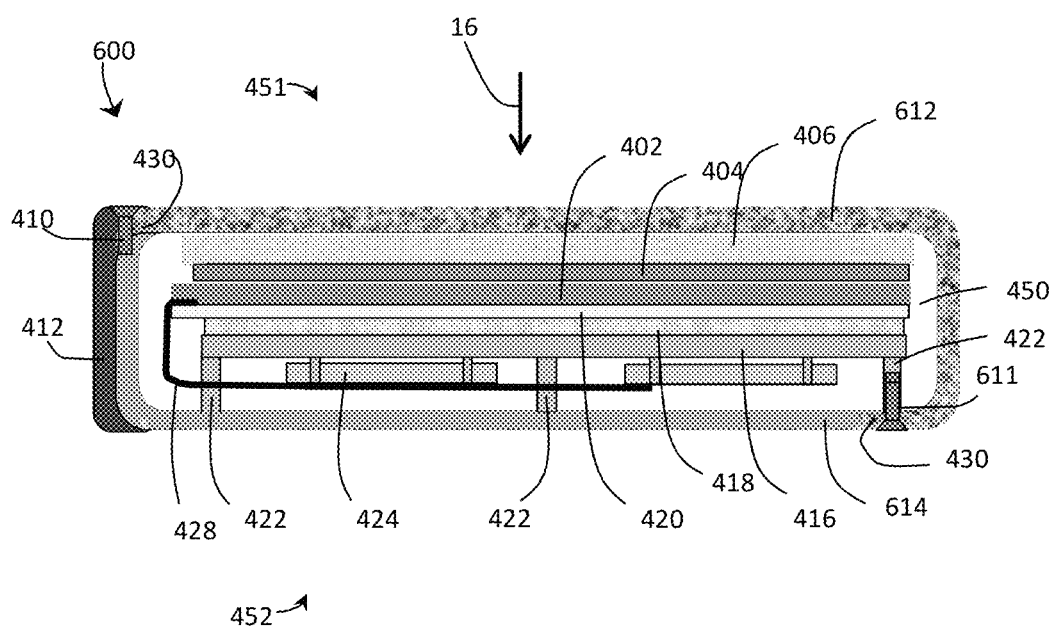
FIG. 6 is a cross-section of a portion of an exemplary portable wireless DR detector according to one embodiment.

FIG. 6 illustrates in schematic form another exemplary cross-section view along section 4-4 of the exemplary embodiment of the DR detector 300 (FIG. 3). Several of the components in the DR detector 600 illustrated in FIG. 6 are similar in most respects to the components as described with respect to the DR detector 400 of FIG. 4 and are identified with the same element numerals. The description of those components bearing the same element numerals is not repeated here. The DR detector 600 comprises a housing 614 having a portion made from a radiopaque material extending along a bottom portion of the DR detector 600 and also continuously forms at least one edge of the housing 614 which, in the perspective of FIG. 6, is located to the left of the interior volume 450. In separate embodiments, the radiopaque portion of the housing 614 may continuously extend long one, two, or three edges of a DR detector 600 having four edges. If the radiopaque portion of the housing 614 extends along two edges, it may extend along any two adjacent and substantially perpendicular edges or along any pair of opposite substantially parallel edges of the DR detector 600.

In the exemplary embodiment of FIG. 6, a portion of the housing 612 is formed from a radiolucent material. This portion of the housing may comprise a continuous extension of the top cover 312 (FIG. 4) to form a portion of the housing 612 for the DR detector 600 that is transparent to x-ray radiation. In separate embodiments, the radiolucent portion of the housing 612 may continuously extend along one, two, or three edges of a DR detector 600 having four edges. If the radiolucent portion of the housing 612 extends along two edges, it may extend along any two adjacent substantially perpendicular edges or along any pair of opposite substantially parallel edges of the DR detector 600. In order to fasten the radiolucent portion of the housing 612, a fastener 611, similar in material and shape as fastener 410, may be used in the bottom side of the DR detector to sealingly fasten the radiolucent edge of the housing 612 to the frame support 416 or to a frame support beam 422. At the edges of the DR detector 600 where the radiopaque housing 614 extends along the edges toward the top side 451, the fastener 410 may be used as described herein to sealingly fasten it to the radiolucent portion of the housing 612. The fastener 611 is positioned in the bottom side 452 to minimize or eliminate placement of any DR detector components that are not radiolucent above, or beyond an edge of, the imaging layer 402 closest to a radiolucent edge of the DR detector 600. This helps to prevent artifacts appearing on radiographic images captured using multiple overlapping DR detectors 600 as described hereinbelow. Similarly, the integrated circuit readout electronics 424 are positioned proximate a (bottom) side of the sensor array imaging device layer 402 that is opposite the x-ray source to minimize or eliminate placement of any electronic components that are not radiolucent above, or beyond an edge of, the imaging device layer 402 closest to a radiolucent edge of the DR detector 600.

Figure 7:
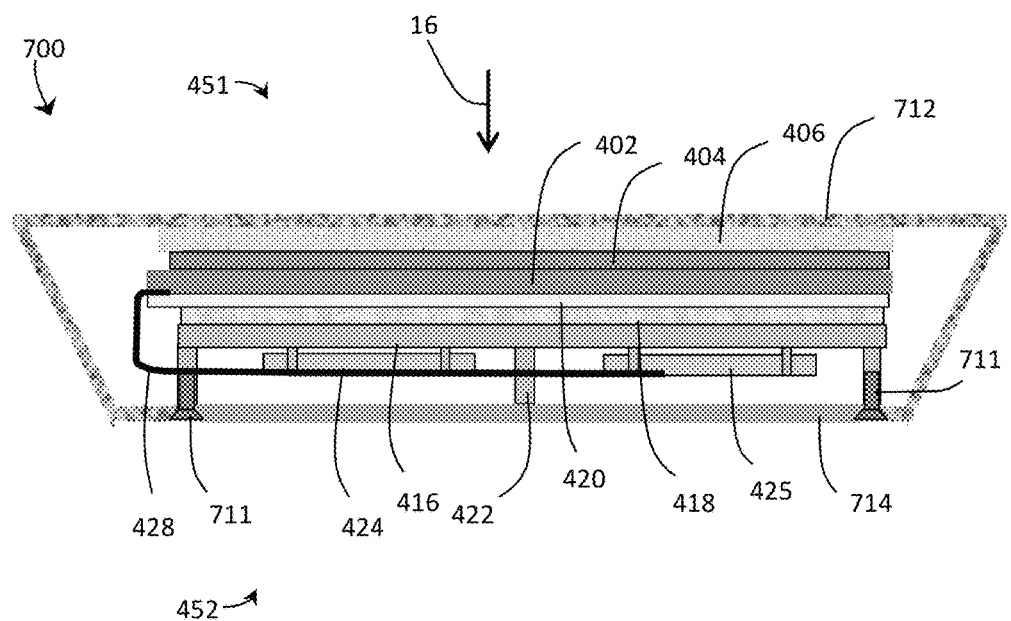
FIG. 7 is a cross-section of a portion of an exemplary portable wireless DR detector according to one embodiment.

FIG. 7 illustrates in schematic form another exemplary cross-section view along section 4-4 of the exemplary embodiment of the DR detector 300 (FIG. 3). Several of the components in the DR detector 700 illustrated in FIG. 7, such as the multilayer structure, are similar in most respects to the components as described with respect to the DR detector 400 of FIG. 4 and are identified with the same element numerals. The description of those components bearing the same element numerals is not repeated here. The DR detector 700 comprises a housing having a portion made from a radiopaque material 714 extending along a bottom portion of the DR detector 700 and may continuously form one or two edges of the housing 714 wherein, in the perspective of FIG. 7, one such edge may be located behind the multilayer structure as depicted therein. In separate embodiments, the radiopaque portion of the housing 714 may continuously extend long one or two edges of the housing 712 of the DR detector 700 having four edges. If the radiopaque portion of the housing 714 extends along two edges, it may extend along opposite edges of the DR detector 700.

In the exemplary embodiment of FIG. 7, a portion of the housing 712 is formed from a radiolucent material. This portion of the housing may comprise a continuous extension of the top cover 312 (FIG. 4) to form opposite edges of the housing 712 for the DR detector 700 that are transparent to x-ray radiation. In separate embodiments, the radiolucent portion of the housing 712 may continuously extend along two, three, or all edges of a DR detector 700 having four edges. In the perspective of FIG. 7, two opposite edges (left and right) are formed from a radiolucent material, such as a carbon fiber reinforced plastic, polymeric, or other plastic based material. The housing 712 may extend vertically between the top side and the bottom side, or it may extend at a non-orthogonal angle therebetween, as shown in FIG. 7. In order to fasten the radiolucent portion of the housing 712, fasteners 711, similar in material and shape as fastener 410, may be used in the bottom side of the DR detector to sealingly fasten the radiolucent edge of the housing 712 to the frame support 416, or to the frame support beam 422, as shown. The fasteners 711, as well as integrated circuit readout electronics 424 are positioned proximate the bottom side 452, which is a side of the sensor array imaging device layer 402 that is opposite the x-ray source to minimize or eliminate placement of any DR detector components that are not radiolucent above, or beyond an edge of, the imaging layer 402 closest to a radiolucent edge of the DR detector 600. This helps to prevent artifacts appearing on radiographic images captured using multiple overlapping DR detectors 700 as described hereinbelow.

Figure 8:
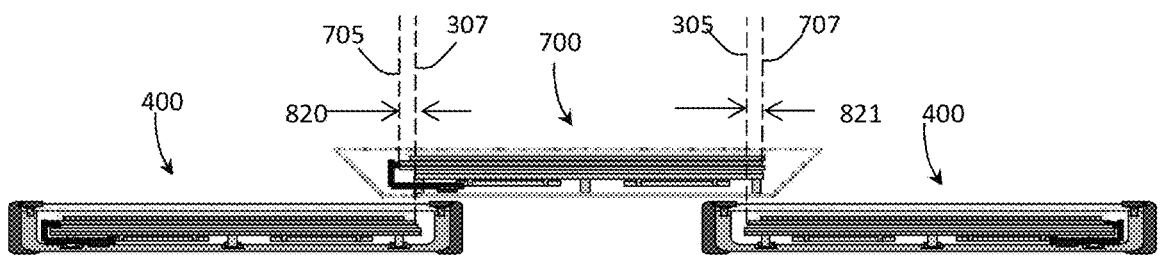
FIG. 8 is a cross-section of an exemplary arrangement of multiple DR detectors in a radiographic imaging system according to one embodiment.

As described herein, DR detector embodiments 400, 600, and 700 are usable individually, as in standard diagnostic radiographic imaging practice, and may be combined, or tiled, as described herein, for long-length imaging. FIG. 8 illustrates a side view of an exemplary arrangement of three DR detectors including two standard DR detectors 400, and a central DR detector 700, as describe herein with reference to FIG. 7, having at least two opposite edges of its housing formed from radiolucent material that each overlap one edge of one of the standard DR detectors 400, as shown. The central DR detector 700 is positioned forward of the standard DR detectors 400 in relation to an x-ray energy source positioned to emit x-rays in a direction as depicted in FIG. 4 and FIG. 7. The central DR detector includes an imaging array layer having one of its edges 705 overlapping an edge of the imaging array layer 307, in a corresponding first one of the standard DR detectors 400, by a distance 820, and an opposite edge of the imaging array layer 707 overlapping an edge of the imaging array 305, in a corresponding second one of the standard DR detectors 400, by a distance 821. The overlapping distances 820, 821 may be equivalent or different. The overlap distance is not critical to the presently disclosed invention, and may range from one or more millimeters to tens or hundreds of millimeters. Because the edges of the DR detector 700 that overlap the edges of the standard DR detectors 400 are radiolucent, and have eliminated or minimized components, such as electronic readout circuits, beyond the edges of the imaging layer 402 therein, a radiographic image captured simultaneously by the three detectors as depicted in FIG. 8, will not include unnecessary artifacts in the portions of the radiographic image captured by the standard DR detectors 400 caused by radiopaque components in the central DR detector 700 that otherwise would be disposed therein beyond the overlapping region if DR detector 700 was configured as a standard DR detector. One advantage of the embodiment depicted in FIG. 8 is that the two prior art standard detectors 400 may be used to capture a long-length image when combined as shown with only one new modified DR detector 700. The embodiment illustrated in FIG. 8 does not require obtaining several DR detectors with modified radiolucent edges. Thus, a radiographic image simultaneously captured by the three DR detectors arranged as in FIG. 8, may be accurately stitched together, without having to mask or process unnecessary artifacts, using standard computer implemented digital reconstruction techniques. Such known digital reconstruction methods include techniques for correcting geometric alignment of images from DR detectors having different source-to-image distance. In the example embodiment shown in FIG. 8, a source-to-image distance of the DR detector 700 may be less than that of the DR detectors 400.

Figure 9:
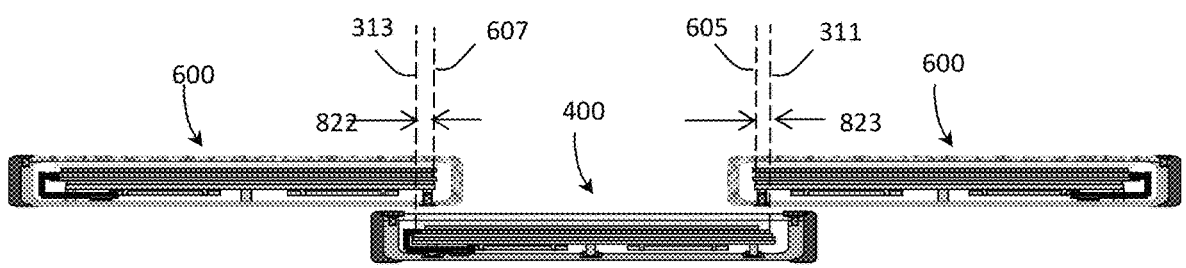
FIG. 9 is a cross-section of an exemplary arrangement of multiple DR detectors in a radiographic imaging system according to one embodiment.

FIG. 9 illustrates a side view of an exemplary arrangement of DR detectors including one standard central DR detector 400, and two DR detectors 600, as described herein with reference to FIG. 6, each having one edge of its housing formed from radiolucent material that overlaps one edge of the standard central DR detector 400, as shown. The central standard DR detector 400 is positioned rearward of the DR detectors 600 in relation to an x-ray energy source positioned to emit x-rays in a direction as depicted in FIG. 4 and FIG. 6. The central standard DR detector 400 includes an imaging array layer having one of its edges 313 overlapped by an edge of the imaging array layer 607 in a corresponding first one of the DR detectors 600 by a distance 822, and an opposite edge of the imaging array layer 311 overlapped by an edge of the imaging array layer 605 by a distance 823 in a corresponding second one of the DR detectors 600. The overlapping distances 822, 823 may be equivalent or different. The overlap distance is not critical to the presently disclosed invention, and may range from one or more millimeters to tens or hundreds of millimeters. Because the respective edge of each of the DR detectors 600 that overlaps the edge of the standard DR detector 400 is radiolucent, and has eliminated or minimized radiopaque components, such as integrated electronic read out circuits, beyond the edge of the imaging layer therein, a radiographic image captured simultaneously by the three detectors as depicted in FIG. 9, will not include unnecessary artifacts in the portion of the radiographic image as captured by the standard DR detector 400 caused by radiopaque components in the DR detectors 600 that otherwise would be disposed therein beyond the overlapping region if DR detectors 600 were configured as standard DR detectors. One advantage of the embodiment depicted in FIG. 9 is that a prior art standard detector 400 may be used to capture a long-length image when combined as shown with two new modified DR detectors 600 each having only one edge modified to be radiolucent. The embodiment illustrated in FIG. 8 does not require obtaining several DR detectors with modified radiolucent edges. Thus, a radiographic image simultaneously captured by the three DR detectors arranged as in FIG. 9, may be accurately stitched together without having to mask or process unnecessary artifacts using standard computer implemented digital reconstruction techniques. Such known digital reconstruction methods include techniques for correcting geometric alignment of images from DR detectors having different source-to-image distance. In the example embodiment shown in FIG. 9, a source-to-image distance of the DR detectors 600 may be less than that of the DR detector 400.

Figure 10:
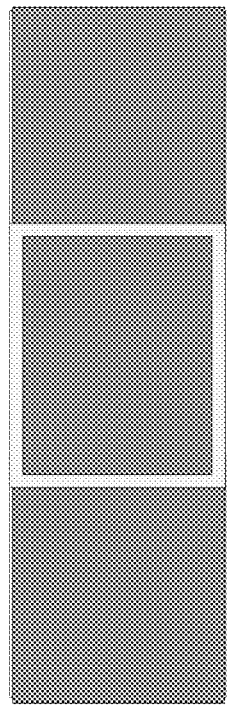
FIG. 10 is a top view of an exemplary arrangement of multiple DR detectors in a radiographic imaging system according to the embodiment of FIG. 8.
Figure 11:
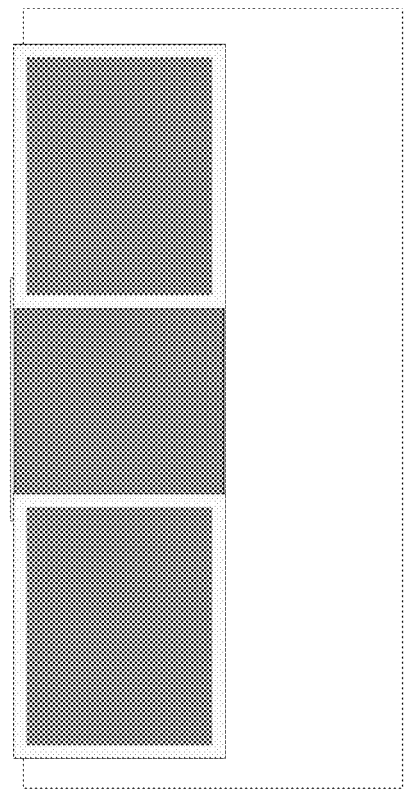
FIG. 11 is a top view of an exemplary arrangement of multiple DR detectors in a radiographic imaging system according to the embodiment of FIG. 9.

FIGS. 10 and 11 illustrate front or top views of the DR detector arrangements as depicted in FIGS. 8 and 9, respectively. As shown, two standard DR detectors 400 are positioned rearward of the DR detector 700 in FIG. 10, in relation to an x-ray source that, in the perspective of FIG. 10, emits x-ray energy toward the page. The DR detector 700, positioned in front, and in the middle, of the two standard DR detectors 400, includes radiolucent edges at its top and bottom edges in the Figure, which overlap the edges of the DR detectors 400, as described in relation to FIG. 8. In FIG. 11, two DR detectors 600, each as described and configured as in the description of FIG. 6, are positioned in front of the standard DR detector 400 in FIG. 11, in relation to an x-ray source that, in the perspective of FIG. 11, emits x-ray energy toward the page. The DR detectors 600 each include at least one radiolucent edge (at least the top or bottom edge) which overlaps a corresponding edge of the middle-positioned standard DR detector 400, as described in relation to FIG. 9. While particular arrangements of DR detectors have been illustrated in FIGS. 8-11, it should be noted that those skilled in the art may envisage that various combinations of DR detectors may be implemented in various geometric combinations. Thus, different types of DR detectors may be utilized in upper, middle, or lower positions, or may be used in combination with four or more detectors, having edges overlapping, wherein each of the DR detectors may be configured to include one, two, three, or four radiolucent edges. Such combinations are considered to be within the scope of the present invention so long as any radiolucent edge of a DR detector is positioned to overlap an imaging array of another DR detector. Radiopaque edges may be positioned rearward of another overlapping DR detector, or may be positioned on an exterior border of the arrangement of DR detectors. Alternatively, some or all of the tiled DR detectors may be arranged in a staggered stepwise fashion (FIG. 13), rather than having one central DR detector positioned forward or rearward of the other detectors.

Figure 12A:
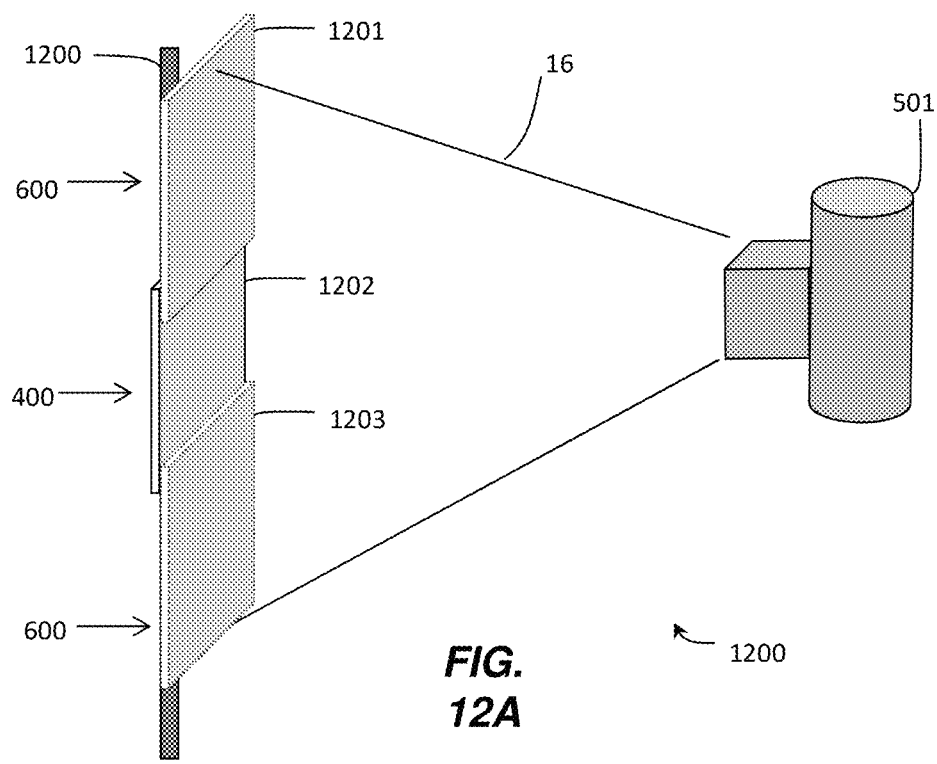
FIG. 12A is a perspective view of an exemplary imaging system implementing an arrangement of DR detectors according to one embodiment.

FIG. 12A illustrates a DR imaging system 1200 using the arrangement of DR detectors as described in relation to FIG. 9 and FIG. 11 for use in a long-length imaging exposure. DR detector 1201 may comprise a wired or wireless DR detector of the type 600 described in relation to FIG. 6; DR detector 1202 may comprise a wired or wireless standard DR detector type of the type 400 described in relation to FIG. 4; and DR detector 1203 may comprise another wired or wireless DR detector of the type 600. X-ray source 501 may be fired once to expose a subject (not shown) to an x-ray beam 16 when the subject is placed between the x-ray radiation source 501 and the multiple DR detectors 1201-1203, to capture a distributed image of the subject that is simultaneously captured and stored by the multiple DR detectors 1201-1203. The captured images, each comprising a portion of the subject, one from each DR detector, may be stitched together using known computer implemented reconstruction techniques to generate a single long-length composite image of the subject. Part of the control operations carried out by the image processing and control unit 34 may include wired or wireless communication with the DR detectors 1201-1203 for verification that the DR detectors have been initiated and are all in a ready state before exposure, for synchronization, and for coordinating storage and identification of image frame data from each of the detectors. Such a method does not require time consuming repositioning of DR detectors 1201-1203, repositioning of the x-ray source 501, or multiple exposures, as may be currently practiced to obtain a long-length radiographic image. The arrangement of DR detectors 1201-1203 may be configured by attachment to a rigid, rollable floor stand structure 1200 using a modified "bucky" arrangement to fix in position each of the DR detectors 1201-1203, or the detectors 1201-1203 may be affixed to a wall mounted structure 1200. Alternatively, the DR detector 1202 may be part of an existing permanent radiographic imaging installation which is fixed in a relative position as shown, while the other two DR detectors 1201, 1203, may be portable DR detectors installed into the mounting structure to be temporarily used for long-length imaging. One embodiment of the present invention may comprise a retrofittable separate structure for temporarily securing in position the DR detectors 1201 and 1203 as shown and allowing movement of the structure having these two detectors 1201, 1203, to position them in front of (overlapping) the fixed installation of DR detector 1202, as will be described below in relation to FIG. 12B. Although the arrangement of DR detectors 1201-1203 has been illustrated as a vertically adjacent alignment wherein the imaging planes of the DR detectors are also vertical, it should be noted that any of the tiled arrangements of DR detectors disclosed herein may be positioned adjacent to each other in a substantially horizontal alignment wherein the imaging planes of the DR detectors are horizontal, such as may be used for a human patient who is lying down on an examination bed with an x-ray source positioned above the patient for full length body imaging, or the DR detectors disclosed herein may be placed adjacent to each other horizontally wherein the imaging planes of the DR detectors are vertical.

Figure 12B:
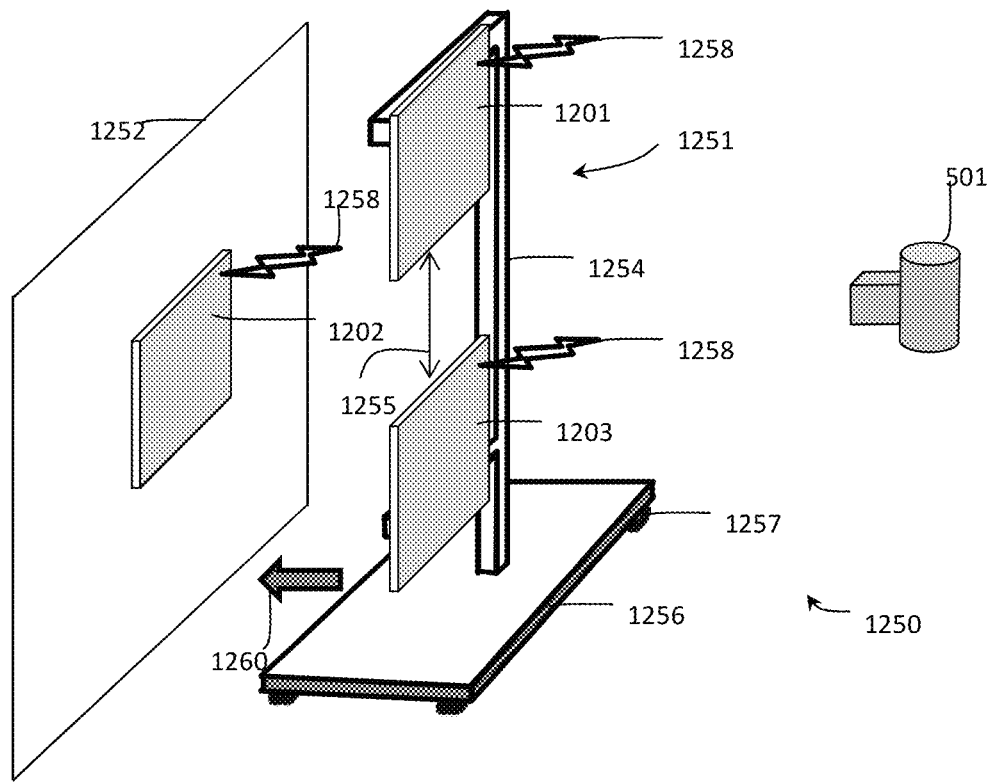
FIG. 12B is a perspective view of an exemplary imaging system implementing an arrangement of DR detectors according to one embodiment.

FIG. 12B illustrates a DR imaging system 1250 using an arrangement of DR detectors as described in relation to FIG. 12A for use in a long-length imaging exposure, except that the DR detectors 1201, 1203 are affixed to a transport apparatus 1251 comprising a support post 1254 attached to a base 1256 outfitted with means for transporting the apparatus 1251 and DR detectors 1201, 1203, such as wheels 1257 which may include freely rotatable wheels, lockable wheels, wheels that may be lowered or raised by hand cranking or by electric motor under operator control, wheels that are not motor-assisted, and motor driven wheels that may be powered by an electric motor to assist in manually transporting the apparatus 1251 by rolling it over a floor or other surface. The support post 1254 secures in a vertical relative position the DR detectors 1201, 1203, using one or more cross-beams attached to the support post 1254, with a preselected gap size therebetween 1255 sufficient for the respective bottom and top edges of the DR detectors 1201, 1203, to overlap a top and bottom edge of DR detector 1202, as previously described. As mentioned above, the DR detector 1202 may represent a standard prior art DR detector permanently installed on one wall 1252 such as in a medical facility imaging room. The DR detector 1202 may be used alone with x-ray source 501 for standard non-elongated radiographic imaging and, in the case where a long-length radiographic image may be desired, the apparatus 1251 may be rolled into position 1260 along a floor of an imaging room. Similarly, DR detectors 1201, 1203, may be portable, to be used individually for performing standard radiographic imaging of patients and may be inserted or attached to support post 1254 to configure the transport apparatus 1251 as described herein. Thus, the portable pair of DR detectors 1201, 1203, may be advantageously affixed to the transport apparatus 1251 to provide a capability to easily convert the permanent installation of the standard DR detector 1202 into the long-length imaging system 1250 when combined as shown with two new modified DR detectors of the type 600 each having one or more edges being radiolucent.

As before, x-ray source 501 may be fired once to expose a subject (not shown) when the subject is placed in front of the multiple DR detectors 1201-1203. Part of the control operations carried out by the image processing and control unit 34 may include wired or wireless communications, wherein wireless communications are represented as wireless transmission signals 1258, with the DR detectors 1201-1203, such as waiting for and synchronizing ready state signals from all activated DR detectors 1201-1203 before an exposure by x-ray source 501. Such a method does not require time consuming repositioning of one or more DR detectors 1201-1203, repositioning of the x-ray source 501, or multiple exposures, as may be currently practiced to obtain a long-length radiographic image.

Figure 12C:
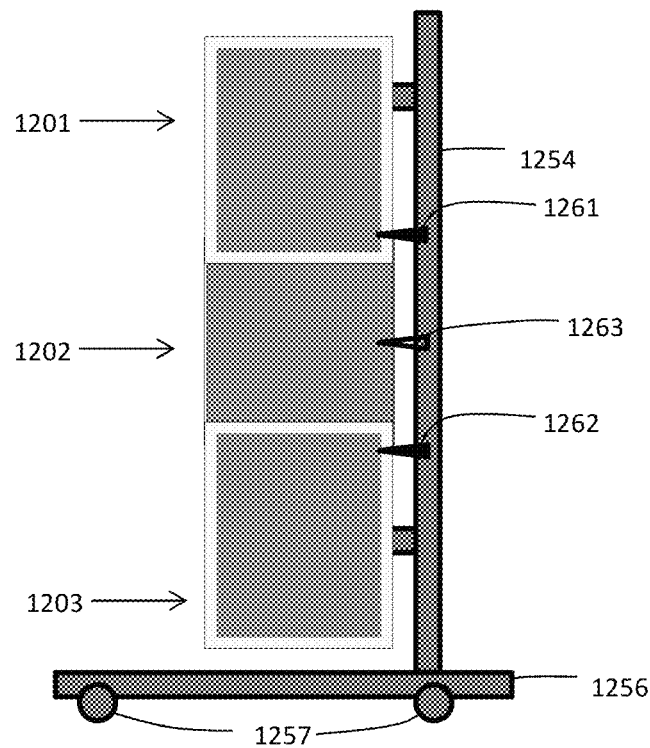
FIG. 12C is a front view of the exemplary transport apparatus of FIG. 12B.

FIG. 12C illustrates a front view of the transport apparatus 1251 of the DR imaging system 1250 of FIG. 12B. Stationary registration markers 1261, 1262, which may be rigidly affixed to support frame 1254, may be used to assist in properly aligning a radiographic image of a subject partially captured by each of two or more detectors 1201-1203. Precision alignment assists in digitally stitching together the captured radiographic images to form an accurate long length radiographic image of the subject. The registration markers 1261, 1262, may be made from a radiopaque material such that a portion of the registration markers 1261, 1262 appear in calibration images captured by the DR detectors 1201-1203. In one embodiment, two partial radiographic images of a subject captured simultaneously by the DR detectors 1201 and 1202 may be precisely aligned using a location of the registration marker 1261 which appears at a particular row of the photosensor array in both calibration images. In another embodiment, two partial radiographic images of a subject captured simultaneously by the DR detectors 1202 and 1203 may be precisely aligned using a location the registration marker 1262 which appears at a particular row of the photosensor array in both calibration images. In another embodiment, three partial radiographic images of a subject captured simultaneously by the DR detectors 1201-1203 may be precisely aligned using locations of the registration markers 1261, 1262, which appear at particular rows of the photosensor arrays in all three calibration images. The row location (e.g. array row number) of the marker 1261 as it appears in the calibration image captured by the detector 1201 may be aligned, for digital stitching purposes, with the row location (e.g. array row number) of the marker 1261 as it appears in the calibration image captured by the detector 1202. Similarly, the row location (e.g. array row number) of the marker 1262 as it appears in the calibration image captured by the detector 1203 may be aligned, for digital stitching purposes, with the row location (e.g. array row number) of the marker 1262 as it appears in the calibration image captured by the detector 1202, thereby allowing the three partial radiographic images of a subject captured simultaneously by detectors 1201-1203 to be precisely aligned and stitched together to form a long length image of the subject.

In an example method embodiment, the detector 1201 may be detached from its cross-beam support and the detector 1202 flashed (exposed without a subject to be imaged) by the source 501 (FIG. 12B) to capture a precise position of the marker 1261 as it appears in such a captured calibration image frame of detector 1202, such as by identifying a precise row, or rows, of the two dimensional array of photosensors where the marker 1261 appears. Thereafter, the detector 1201 may be reattached to its cross-beam support and similarly flashed by the source 501 to capture a precise position of the marker 1261 as it appears in the captured calibration image frame of detector 1201, such as by identifying a precise row, or rows (depending on photosensor resolution), of the two dimensional array of photosensors where the marker 1261 appears. Such flash exposures may also be used to capture a correction image, or correction map, of the detector's photosensor array such as a gain correction map to be used for final image correction, as described hereinbelow.

A subject to be radiographically imaged may be positioned between the detectors 1201, 1202 and the x-ray source 501, and exposed by the source 501 whereby radiographic images of the subject are captured by detectors 1201 and 1202. The radiographic exposure and image capture of the subject may take place before or after the calibration images are captured. The markers 1261-1263 may be configured to be removable or not, and may be removed prior to radiographic imaging of the subject, if desired. The captured radiographic images of the subject can then be digitally stitched together to form a long length image, using well known techniques, relying upon the precise overlap position of the marker 1261 in each corresponding photosensor row of the images as determined by the captured calibration images. The identified row in the radiographic image captured by detector 1201 may be overlapped precisely on the identified row of the radiographic image captured by the detector 1202 to determine an exact overlap alignment of the images. In a similar process, a long length radiographic image of a subject may be formed using the detectors 1202 and 1203 and marker 1262. Similarly, all three detectors 1201-1203 and the both markers 1261-1262, may be used to capture calibration images, whereby a three detector exposure and image capture of a subject may be used to form an even longer length radiographic image comprising radiographic images from all three detectors digitally stitched together. In an example method using three detectors 1201-1203, the detector 1202 may be flashed with both markers 1261 and 1262 captured in its calibration frame (while detectors 1201, 1203 are removed from the support frame 1254) to determine in which rows the markers 1261 and 1262 appear, and thereafter each detector 1201 and 1203 may be replaced onto the support frame 1254 and flashed to form their calibration images and to determine the row location of marker 1261 in the calibration image of detector 1201, and the row location of marker 1262 in the calibration image of detector 1203. The three captured radiographic images of the subject can then be digitally stitched together to form a long length image, using well known techniques, relying upon the identified overlap row locations of the markers 1261 and 1262 in each corresponding photosensor row of the overlapping images, as described above.

In another embodiment, radiopaque markers 1261, 1262, may be rigidly affixed to support frame 1254 at precisely the top and bottom row locations of the photosensor array of detector 1202. In this embodiment, calibration images may not be required to determine a row position of any of the markers 1261, 1262 in the calibration images. The markers 1261, 1262 may each be positioned such that it appears proximate an edge of a captured radiographic image of a subject. Because the markers 1261, 1262, are radiopaque they may appear in the radiographic images of the subject as white areas or points in the image. As shown in FIG. 12C, a tip of marker 1261 would appear proximate an edge of a radiographic image of a subject captured by detector 1201 and a tip of marker 1262 would appear proximate an edge of a radiographic image of a subject captured by detector 1203. Because the precise location of the markers 1261, 1262, appearing in the subject radiographic images are known to be aligned with the top and bottom rows of the photosensor array of detector 1202, a precise row overlap of the captured radiographic images of the subject as between the detector 1202 and either or both of the subject radiographic images captured by detectors 1201 and 1203 can be obtained to digitally stitch together a long length image of the subject. As detailed in the methods disclosed above, any two adjacent detectors, or all three detectors, may be used to capture a long length radiographic image of the subject.

In another embodiment, a radiopaque marker 1263 may be rigidly affixed to support frame 1254 in a similar manner as radiopaque markers 1261-1262. The markers 1261-1263 may be affixed to support frame 1254 at precisely known distances from each other. In this embodiment, calibration images may not be required to determine a row position of any of the markers 1261-1263 in the calibration images. The markers 1261-1263 may each be positioned such that it appears proximate an edge of a captured partial radiographic image of a subject. As shown in FIG. 12C, marker 1261 would appear proximate an edge of a radiographic image of a subject partially captured by detector 1201. Similarly, marker 1262 would appear proximate an edge of a partial radiographic image of a subject captured by detector 1203, and marker 1263 would appear proximate an edge of a partial radiographic image of a subject captured by detector 1202. Because the precise distance between the markers 1261-1263 are known, any of the markers 1261-1263 appearing in the partial radiographic images of the subject may be used to precisely overlap the images by a known amount and digitally stitch together the partial captured radiographic images to form a complete long length image. Although the sizes of the markers 1261-1263 in FIG. 12C may be exaggerated, as illustrated, for clarity, their sizes may vary. In one embodiment, the marker may be a small rod, or it may be as small as a fine wire or needle. The marker may be permanently affixed to the detector or to the support structure that secures the detector in place, or it may be insertable through an opening in a side wall of the detector such as by snapping it into place or threading it through a screw hole, for example. As described in the methods above, any two adjacent detectors, or all three detectors, may be used to capture a long length radiographic image of a subject.

In one embodiment, the detectors 1201-1203 may be secured in position for radiographic imaging of a subject and flashed by the x-ray source 501 to capture an offset calibration image whereby the overlapping detector's attenuation of x-rays impacting a portion of the overlapped photosensor array is captured by the overlapped detector. Such a calibration image may be referred to as an overlap gain map, or overlap gain correction image.

Other correction images may also be captured and stored by the detectors 1201-1203 as correction maps for the photosensor array, such as gain maps or offset maps, which are then combined with captured radiographic images during image finalization to correct for deviations in individual imaging pixels of the photosensor array. As described above, the markers 1261-1263 may be also be used to align one or more correction maps captured by the detectors 1261-1263. The apparatus and methods of operating the radiographic imaging systems described herein with respect to obtaining and using correction maps are described in more detail hereinbelow.

FIG. 13 illustrates an embodiment of a DR imaging system 1300 wherein more than three DR detectors are positioned in an overlapping fashion to capture a long-length radiographic image. X-ray source 501 may emit a single radiographic energy pulse that is received and captured by DR detectors 1301-1305 as shown. A subject positioned in front of the DR detectors 1301-1305 may result in radiographic images being generated in the DR detectors 1301-1305, each comprising a portion of a radiographic image of the subject using the single radiographic energy pulse. As shown, DR detector 1301, the uppermost DR detector as shown, is illustrated as a DR detector 600 as described herein with reference to FIG. 6. Because DR detector 1301 is not positioned forward of another DR detector, it may alternatively comprise a standard DR detector such as the DR detector 400 described in relation to FIG. 4. Moreover, DR detector 1301 may comprise a DR detector such as the DR detector 700 described in relation to FIG. 7. Such alternate configurations are considered to be encompassed by the present disclosure because they embody preferred configurations wherein a radiopaque edge of any DR detector used does not overlap the imaging array of another DR detector positioned behind it. In similar fashion, DR detector 1302, second from the top as shown, may comprise a detector of the type described in relation to FIG. 7 wherein opposite edges (top and bottom edges in the perspective of FIG. 13) are configured to be radiolucent; DR detector 1303, third from the top as shown, may comprise a standard DR detector 400 of the type described in relation to FIG. 4, or it may comprises a DR detector 600 or 700 as described in relation to FIG. 6 and FIG. 7, respectively; DR detector 1304, fourth from the top as shown, may comprise a DR detector 600 as described in relation to FIG. 6 wherein only its upper edge is configured to be radiolucent; and DR detector 1305, at the bottom of the arrangement as shown, may similarly comprise a DR detector 600 as described in relation to FIG. 6 wherein only its upper edge is configured to be radiolucent. The detectors 1303-1305 are positioned in a staggered stepwise arrangement, which stepwise arrangement may comprise an alternative arrangement for all the DR detectors 1301-1305, as desired. As shown, the DR detectors 1301-1305 may be fixed to a support structure 1300 for securing in position the DR detectors 1301-1305.

Figure 14C:
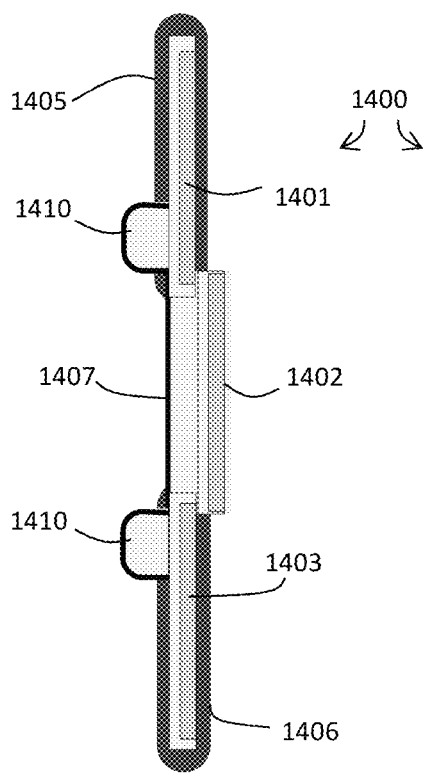
FIG. 14C-D are a side view and front view, respectively, of the exemplary bucky apparatus of FIG. 14B as assembled, according to one embodiment.
Figure 14D:
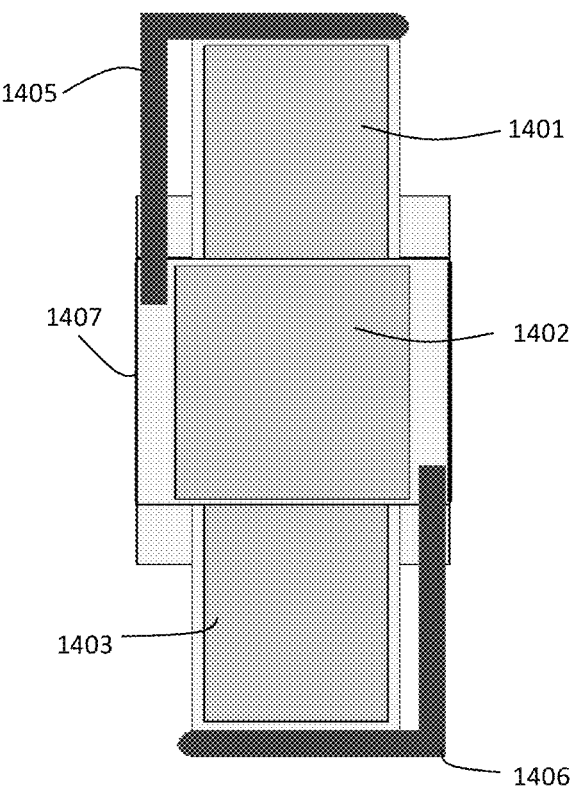

FIG. 14A-14D illustrate a bucky apparatus 1400 that includes a retractable frame to allow positioning of two or more DR detectors adjacent to each other for radiographic image capture. As shown in FIG. 14A, bucky apparatus 1400 may be attached to a wall, to a transport apparatus 1251 (FIG. 12C), or the bucky apparatus 1400 may be attached to a bed in a horizontal orientation. The bucky base 1407 may also include attachment portions 1410 (FIG. 14C) to assist in securing the bucky apparatus to a wall or to the crossbeams of transport apparatus 1251. The bucky apparatus 1400 may used to support a single DR detector 1402 in an imaging orientation, such as shown in FIG. 14A, using frame members 1405 and 1406, during radiographic imaging of a subject. The frame members 1405-1406 may be slidably connected to a bucky base 1407 that allows frame members 1405-1406 to be both or individually moved apart, in the directions shown by the arrows in FIG. 14A, while the bucky base 1407 secures detector 1402 in place, as shown in FIG. 14B. Upon separating one or both of the frame members 1405, 1406, one or both of additional detectors 1401, 1403, may be inserted into one or both the frame members 1405, 1406, respectively, in the directions shown by the arrows in FIG. 14B, so that the one or both inserted detectors 1401, 1403, are secured in a vertically adjacent position with respect to the detector 1402. It should be understood that the bucky apparatus 1400 may be configured to allow, in one embodiment, the additional one or both detectors 1401, 1403, to be secured in position in front of the detector 1402 and, in another embodiment, to be secured in position behind the detector 1402 as shown in FIG. 14B. In either embodiment, appropriate detector constructions as exemplified and described in relation to FIGS. 8-9 herein may be selected. It should also be understood that the bucky apparatus 1400 may be configured with markers similar to markers 1261-1263 as described in relation to FIG. 12C. Thereby, in an exemplary three-detector embodiment, the fully assembled bucky apparatus 1400, as shown in the side view of FIG. 14C and the front view of FIG. 14D, may be used for long length imaging in combination with the methods and configurations described herein.

Figure 15:
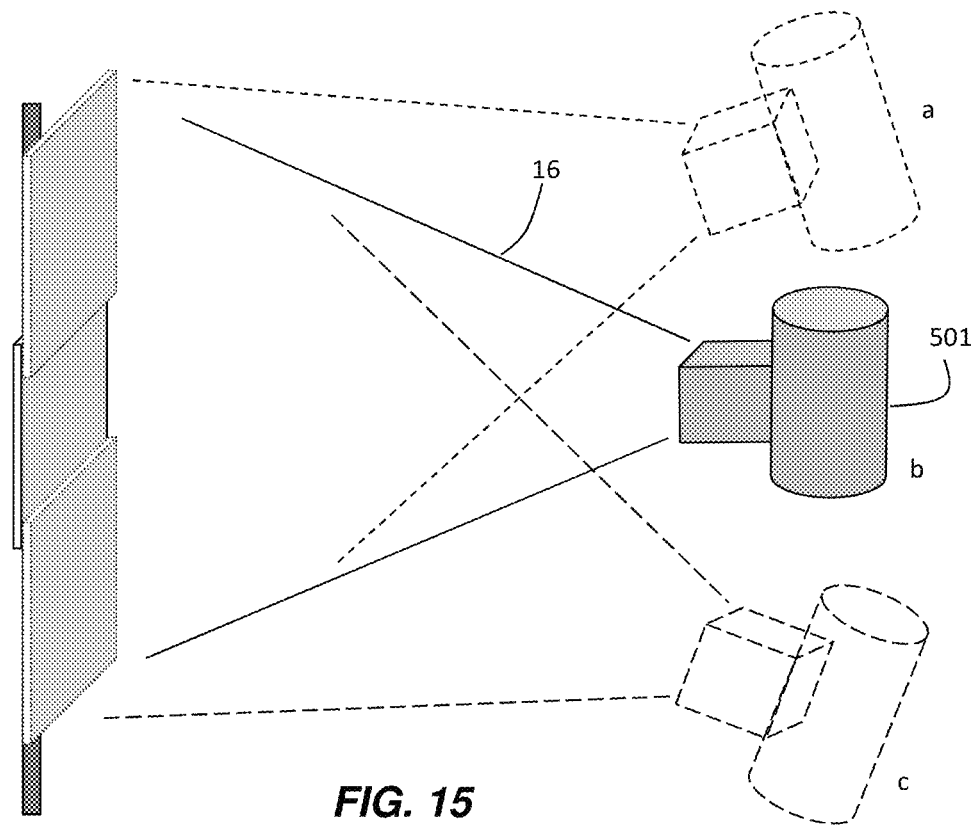
FIG. 15 is a perspective view of an exemplary imaging system implementing an arrangement of DR detectors according to one embodiment.

FIG. 15 illustrates a method of capturing radiographic images of a subject to be used in generating tomosynthesis images of a subject. The arrangement of the multiple DR detectors in this example, i.e., three detectors, to the left of FIG. 15 is adequately described herein, such as in reference to FIG. 12A, and is not repeated. The x-ray source 501 may be configured to be translatable in a vertical direction in relation to the three detector array such that each firing of the x-ray source 501 at the positions a, b, c, emits an x-ray beam 16 that exposes all of the multiple detectors simultaneously. Although only three exemplary positions of the x-ray source 501 are shown, the source 501 may be positioned and fired from any number of positions, such as fifteen or thirty positions. The x-ray source 501 may be attached to a vertical structure, such as a vertical rail (not shown), that is used to translate the x-ray source linearly while adjusting an aim of the x-ray beam 16 toward the array of multiple detectors. In one embodiment, the x-ray source 501 may be movably attached to an arc shaped rail (not shown) having a curvature that points the x-ray beam 16 toward the detectors as the x-ray source moves along the arc shaped rail. In the embodiment of FIG. 15, preparatory flash images, as described herein, may be captured by each of the detectors at each of the different positions of the x-ray source 501. The prepatory flash images may be required due to the varying overlap attenuation distances caused by the top and bottom detectors overlapping the middle detector as the x-ray source is translated. The varying overlap attenuations may be compared, in certain respects, to a varying x-ray shadow projected by the bottom edge of the top DR detector onto the middle DR detector and by the top edge of the bottom detector onto the middle detector. Hence, an overlap gain correction that may be applied to the middle detector will vary for each position of the x-ray source. Such overlap gain correction images may be captured by the middle DR detector at each position of the x-ray source 501 during a preparatory stage when the x-ray source 501 may be flashed at each position that will be used for an actual subject tomosynthesis image exposure. The overlap gain correction images can then be stored and later used to adjust (gain correct) the corresponding subject radiographic image. Alignment and stitching procedures for radiographic images captured using the embodiment of FIG. 15 may be implemented using any of the methods as disclosed herein.

Figure 16:
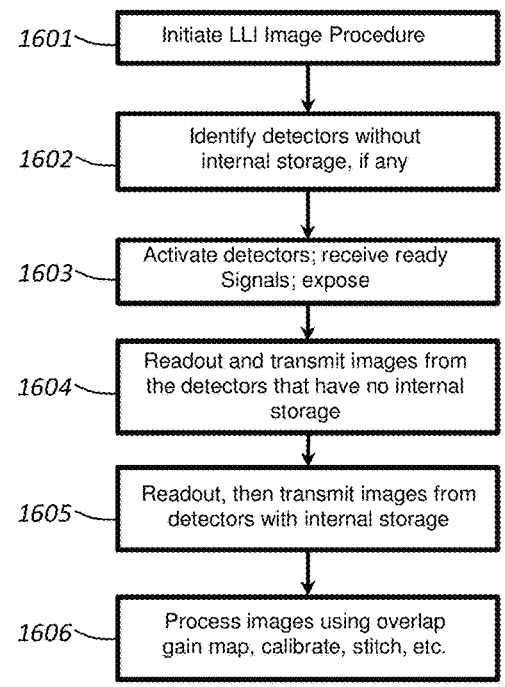
FIG. 16 is a flow chart of an exemplary method of operating a multi-detector imaging system.

FIG. 16 is an exemplary flow chart that illustrates methods of operating a radiographic imaging system 10 as disclosed herein which include two or more DR detectors used to capture long length radiographic images of a subject. With reference to FIG. 16, a multi-detector imaging system may be initialized, at step 1601, by installing DR detectors into an imaging arrangement, such as by attaching or inserting two or more detectors into a wall stand, bucky, a single housing or imaging assembly, or the transport apparatus 1251, for example, as described herein. A calibration procedure may then be performed that includes flashing the detectors using an x-ray source to capture calibration or correction images as well as registration or geometric alignment information. A forward positioned detector, which is not overlapped and receives full x-ray exposure, may use the flash step to capture and store a gain correction image to be used later during a subject image finalization process.

A detector positioned rearward, which is overlapped by a forward positioned detector, may use the flash step to capture an overlap gain correction image to be used for overlap gain adjustment, or compensation, for those imaging pixels in the overlapped detector that receive x-rays attenuated by structures within the forward positioned detector, and thus undergo a gain loss. Such overlapping structures may include one or more of a housing, such as a carbon fiber housing which is considered to be generally radiolucent but which may nonetheless attenuate an x-ray to some extent, electronic components, an edge of the photosensor array, a scintillator layer whose thickness may vary, a glass layer, and other components. Any one or more of these attenuating components may extend beyond an edge of the photosensor array of the forward positioned detector. In this manner, by flashing the detectors, registration and overlap gain correction images may be obtained and stored for the multi-detector arrangement. The amount of x-ray energy received in the rearward detector photosensors may vary over some unit distance in any direction in the rows and columns of photosensor imaging pixels. Thus, the overlap gain image is advantageous in mapping the energy attenuation pattern precisely as detected by the rearward positioned detector. The attenuation magnitude may be determined by comparing an x-ray intensity that is expected in a fully exposed photosensor (as determined by, e.g., calibration exposures)

with the attenuated intensity, and using that difference to thereby adjust the corresponding imaging pixel in a captured image during gain correction. In addition, positions of any markers as described herein may be obtained and recorded. Because the positions of the detectors and/or the x-ray source may vary between successive imaging sessions, the flash step may be performed just before each actual exposure of a subject to insure proper registration and gain correction.

At step 1602, it may be necessary to identify if any of the multiple detectors to be used for subject radiographic imaging are without internal electronic storage. In such an embodiment, it may be necessary for the host system to record which detector does not contain storage for image data and to be prepared to receive read out image data from such a detector immediately after exposure begins. Such a detector may be electrically connected to the host system by wire or cable and so the captured image data may be transferred thereby. In one embodiment described herein with respect to FIG. 12C, the middle-positioned detector 1202 may be permanently attached to, for example, a wall stand as part of a legacy imaging system, may not include internal storage for images, and may electronically communicate with a host processing system wirelessly or by cable. In one embodiment, the middle-positioned detector 1202 may be a CR detector that is manually removed and carried to a reader used to decode a phosphor plate. Digital wireless radiographic detectors 1201, 1203, may be attached to a transport apparatus 1251, as described herein, as a retrofit to the existing wall stand detector 1202 to enable long length imaging. In this embodiment, the digital wireless detectors 1201, 1203, may include on-board processing and/or electronic memory for processing and storing captured radiographic images, as described herein with reference to FIG. 1, which may then be transferred out at a later time. Thus, the subject image data captured by detector 1202 will have to be read out first, before retrieving image data from detectors that have electronic storage for captured image data, in this embodiment. Information regarding which detector does not contain internal storage is determined before x-ray exposure begins as part of initializing the imaging system.

At step 1603, the imaging system transmits activation signals to the multiple detectors to place the detectors into a ready state for image capture. A host processor, for example, then waits to receive a ready signal from all the detectors that are equipped to transmit a ready signal and which will be used for image capture. After all the expected ready acknowledgments are received, the x-ray source is triggered for exposure. The multiple detectors each capture a portion of a radiographic image of the subject in response to a single x-ray exposure. At step 1604, a detector without digital memory for storing the captured image, if any, reads out and transmits the image data, such as via a connected cable or wirelessly, to the host processing system and the captured image is then stored and processed in the host system. Simultaneously, indicated at step 1605, detectors having on-board electronic memory for storing the captured radiographic image may read out and store internally the captured image data until instructed to transmit, or transfer, the image data, by cable or wirelessly, to the host system. At step 1606, such detectors may also initiate on-board programming for defect concealment or other error corrections, offset correction, gain correction, and other image processing functions to generate final viewable image data, or such image processing functions may be performed at the host system. Stitching together the multiple images captured by the detectors to form a long length image may be performed at the host system which has received and stored all the associated captured radiographic images. In particular, the host system may utilize an overlap gain map to compensate individual pixel's image data captured in overlapped pixels as described herein. The host system may also use row identifiers providing precise row overlap positions of the images captured by overlapping detectors for proper geometric alignment when digitally stitching together the captured images in order to form the long length image.

Figure 17A:
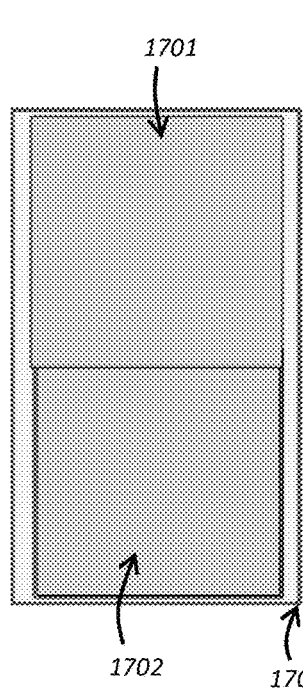
FIGS. 17A-B are schematic diagrams of exemplary DR LLI assemblies.
Figure 17B:
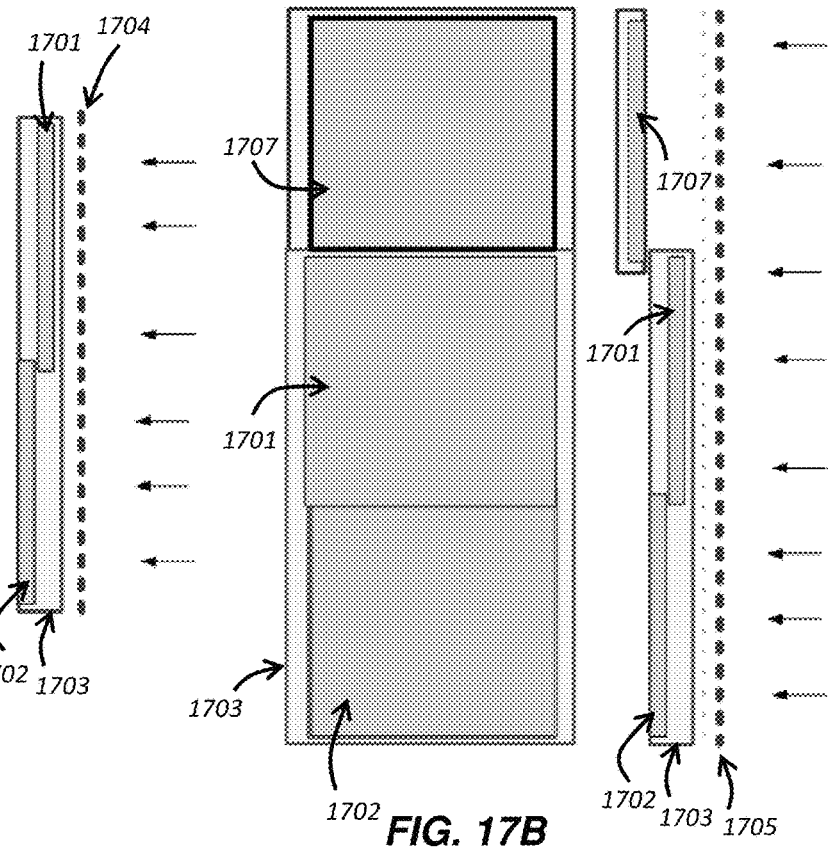

FIGS. 17A-B are each schematic front and side views of first and second detectors 1701, 1702, arranged in an overlapping fashion within a single housing 1703. As shown, the upper detector 1701 is positioned in front of the lower detector 1702, in relation to an x-ray source (not shown). The side of the housing 1703 facing the x-ray source may include a double sized grid 1704 attached thereto. As shown in FIG. 17B, an optional third detector 1707 may be arranged above the pair of detectors 1701, 1702, to increase a size of a long length DR image of a subject captured simultaneously in all three of the arranged DR detectors 1701, 1702, 1707. As described herein above, a detector, such as detector 1701, that is positioned forward (in front of) overlapped detectors, such as detectors 1702 and/or 1707, may include radiolucent material to form the overlapping edge or edges thereof. The side of the three detector configuration housing (front) facing the x-ray source may include a triple sized grid 1705 attached thereto.

Figure 18:
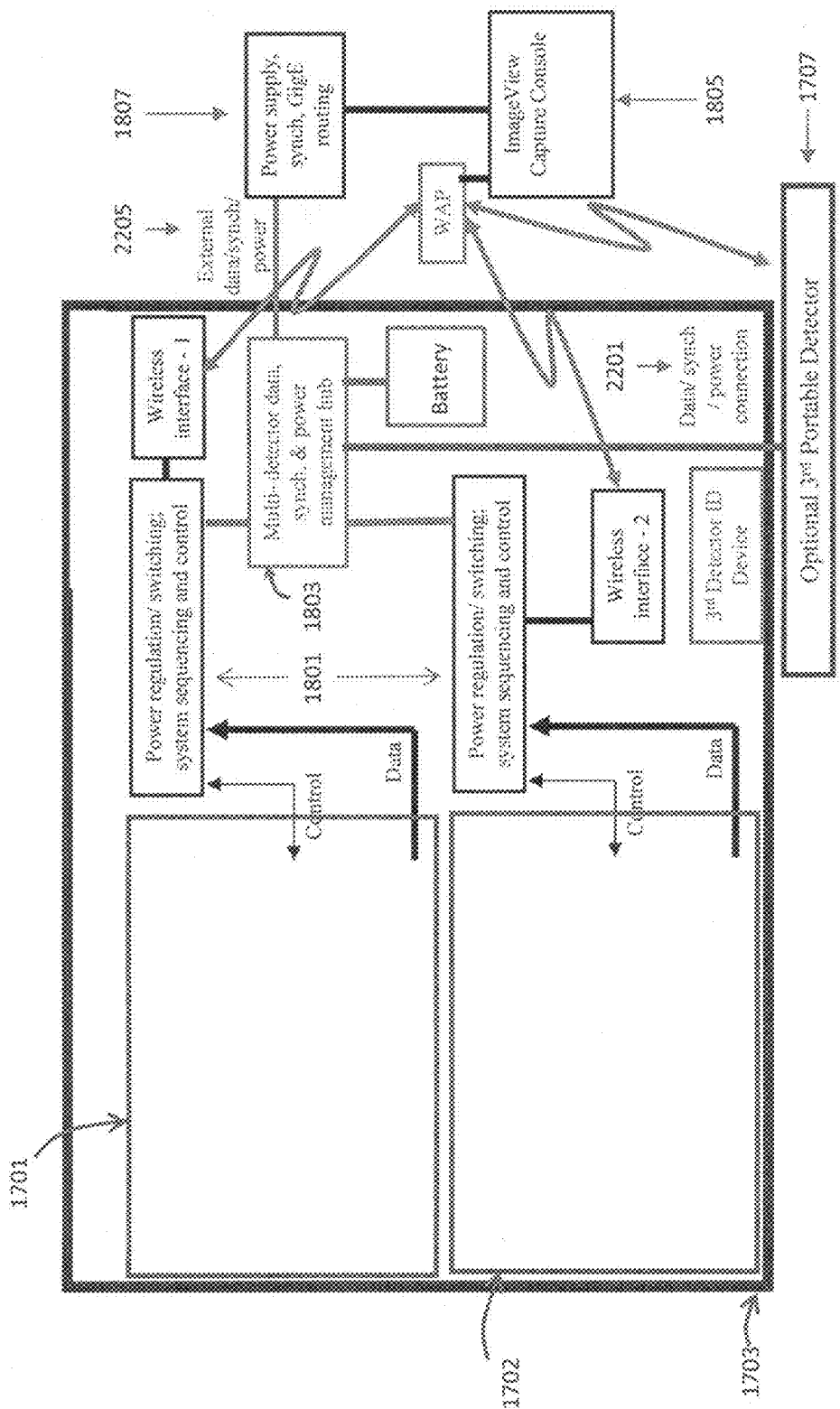
FIG. 18 is a functional block diagram of an exemplary DR LLI assembly.

FIG. 18 is a functional block diagram of an imaging assembly comprising two DR detectors 1701, 1702, as described herein, enclosed within a housing 1703. Each of the DR detectors 1701, 1702, is electrically connected to a separate power regulator 1801, which, in turn, are electrically connected to a power management hub 1803. The power regulator 1801 controls powering-up of two or three detectors in the imaging assembly and their data processors, controls refresh operations and data processing sequencing among the two or three detectors, and maintains full operation of the imaging assembly. The power management hub 1803 is electrically connected to a power source such as an on-board battery, or an external power supply provided via hub 1807 which may include an external battery or a main medical facility power source. The power management hub 1803 manages a single energy input, either power supplied from a battery or from an external power facility supply via hub 1807, and manages distribution of power to two or three detectors for normal operations or for charging a battery in the imaging assembly. The power management hub 1803 also controls a single external connector 2205 (FIGS. 22A, B, D) to manage wired communication among two or three detectors with an external network console 1805. The power source used provides sufficient power for all operations performed by the DR detectors 1701, 1702, and the imaging assembly. Each of the DR detectors 1701, 1702, include a wireless interface having a transmitter/receiver for wireless communications with imaging console 1805, via a wireless access point (WAP) connected to the imaging console 1805. Each of the DR detectors 1701, 1702, may be electrically connected to the imaging console 1805 via a cable that carries power and data through a hub 1807 using a network protocol such as an Ethernet protocol. One feature of the imaging assembly makes use of a single external connector 2205 (FIGS. 22A, B, D) providing an electrical connection to external sources for power transmission and Ethernet data communication. The imaging console 1805 includes a processing system for controlling operation of the imaging assembly, synchronization of image captures by the detectors 1701, 1702, x-ray source firing, image transmission and image processing. A third detector having an electrical connector 2202 (FIG. 23D) thereon may be electrically connected to the imaging assembly via a mating electrical connector 2201 (FIGS. 22A, D) on the housing 1703. This electrical connection merges the third detector 1707 into the imaging assembly for purposes of simultaneous LLI capture and system communication and sequencing, whereby the third detector 1707 shares in receiving power distribution and wired and wireless data communication with the console 1805.

Figure 19:
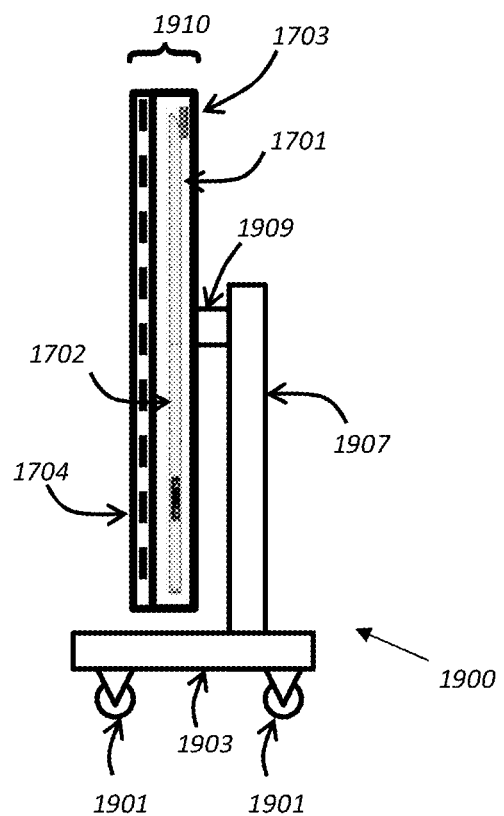
FIG. 19 shows a side view of an exemplary DR LLI mobile system.
Figure 20:
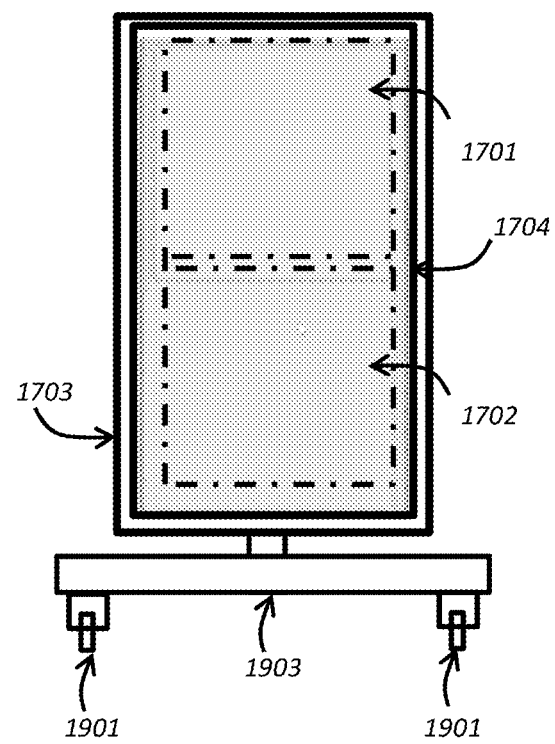
FIG. 20 shows a front view of the exemplary DR LLI mobile system of FIG. 19.

FIGS. 19-20 are side and front view schematic diagrams, respectively, showing the double imaging assembly 1910 of two detectors 1701, 1702, secured within extendable housing 1703, as described herein with relation to FIG. 17A. With reference to FIGS. 19 and 20, a double sized grid 1704 may be attached to a front side of the housing 1703. The double imaging assembly 1910 may be attached to a movable imaging cart 1900 comprising a base section 1903 having wheels 1901 for rolling the imaging cart 1900 over a surface such as a floor. A vertical column 1907 is attached to the base 1903. A horizontal arm 1909 is attached to the column 1907 and to the double imaging assembly 1910. The horizontal arm 1909 may be extendable and retractable in a horizontal direction away from and toward the vertical column 1907, such as being fabricated in a telescoping configuration. The horizontal arm may be attached to the double imaging assembly 1910 via a joint that is rotatable in at least two dimensions, and preferably in three dimensions as described herein below.

FIGS. 21A-B are side and front view schematic diagrams, respectively, showing the triple imaging assembly 1920 of three detectors 1701, 1702, 1707, secured within extendable housing 1703 extended to enclose an additional third detector 1707, as described herein with relation to FIG. 17B. With reference to FIGS. 21A-B, a triple sized grid 1705 is attached to a front side of the extended housing 1703. The triple imaging assembly 1920 may be attached to a movable imaging cart 1900 comprising a base section 1903 having wheels 1901 for rolling the imaging cart 1900 over a surface such as a floor. A vertical column 1907 is attached to the base 1903. A horizontal arm 1909 is attached to the column 1907 and to the triple imaging assembly 1920. The horizontal arm 1909 may be extendable and retractable in a horizontal direction away from and toward the vertical column 1907, such as being fabricated in a telescoping configuration. The horizontal arm may be attached to the triple imaging assembly 1920 via a joint that is rotatable in at least two dimensions, and preferably rotatable in three dimensions as described herein below.

FIGS. 22A-B are perspective views of the housing 1703 enclosing two detectors 1701, 1702, therewithin, and FIGS. 22C-D are front and rear views thereof, respectively. A rear side of the housing 1703 is facing upward in the perspective views of FIGS. 22A-B. The housing 1703 is configured to be attached to a third detector 1707. The housing 1703 comprises a lip 2203 made from a radiolucent low attenuation material extending from the main body of the housing 1703 to assist in a blind insertion of a third detector 1707 as described herein. The radiolucent low attenuation material of the lip 2203 may overlap a third detector in a three detector embodiment (FIGS. 23A-D). One edge of the third detector 1707 rests against the surface 2207 of the housing 1703 when the triple imaging assembly 1920 is assembled. An electrical connector 2201 in the housing 1703 is configured to electrically engage a mating connector of the third detector 1707 when assembled, which electrical engagement allows power and wired data transmission and synchronization as explained above with reference to FIG. 18. A single external connector 2205 is electrically coupled to two or three detectors and enables power and wired data transmission (Ethernet) between two or three detectors and an external processing system (console) when the external processing system is electrically coupled to connector 2205.

Figure 23A:
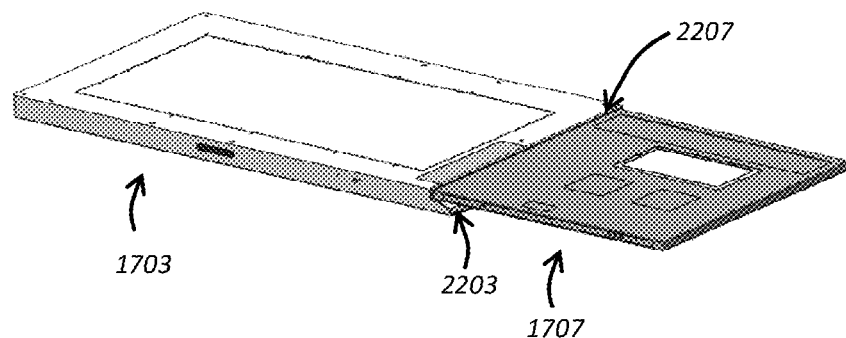
FIGS. 23A-D illustrate various views of another exemplary DR LLI assembly.
Figure 23B:
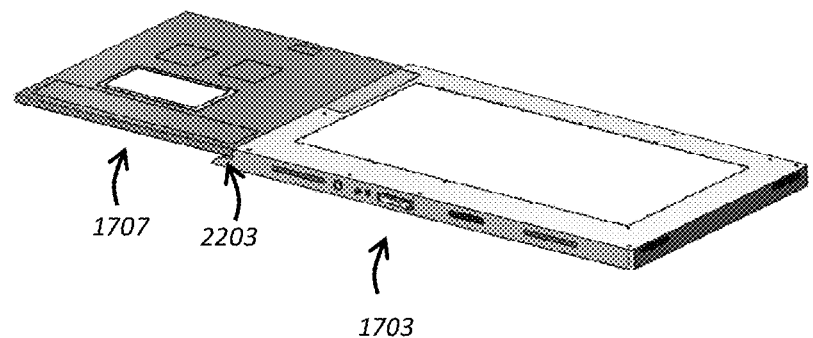
Figure 23C:
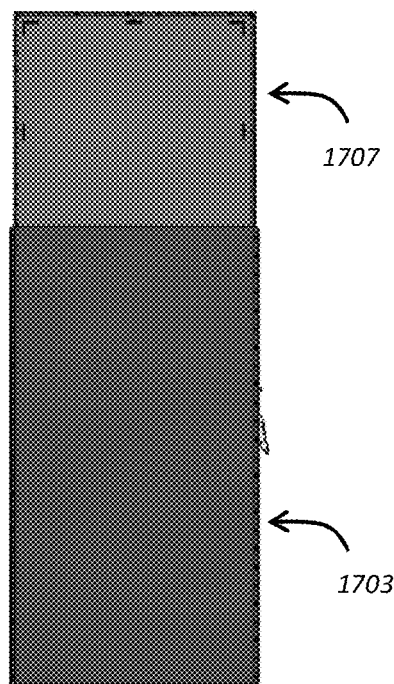
Figure 23D:
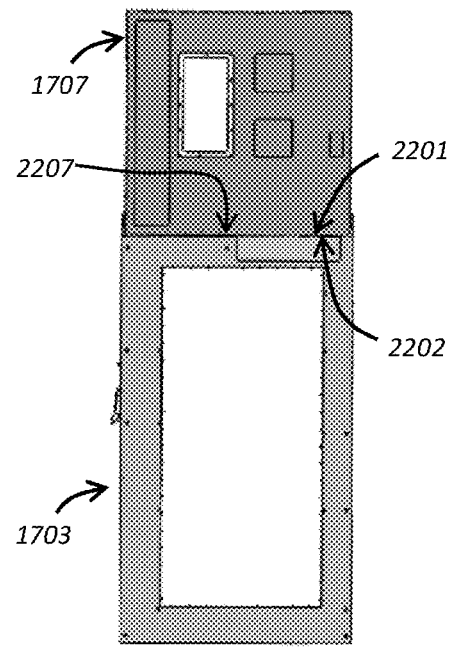

FIGS. 23A-B are perspective views of the housing 1703 enclosing two detectors 1701, 1702, therewithin, electrically attached to a third detector 1707, and FIGS. 23C-D are front and rear views thereof, respectively. A rear side of the housing 1703 and detector 1707 is facing upward in the perspective views of FIGS. 23A-B. The third detector 1707 abuts the radiolucent lip 2203 extending from housing 1703 as well as a surface 2207 of the housing 1703. One edge of the third detector 1707 rests against the surface 2207 of the housing 1703 as shown in FIGS. 23A-D when the triple imaging assembly 1920 is assembled as described herein. An electrical connector 2201 in the housing 1703 is configured to electrically engage a mating connector 2202 of the third detector 1707 when assembled, which electrical engagement allows power and data transmission as well as synchronization among the three detectors 1701, 1702, 1707, as explained above.

FIGS. 24A-E are perspective views of the imaging cart 1900 having an assembled double imaging assembly 1910 attached thereto as described above in relation to FIGS. 19-20. The extendable housing 1703 having an extendable top portion 2401 encloses two detectors 1701, 1702, and includes an attached double sized grid 1704 on the front of the housing 1703. As described above in relation to FIGS. 19-20, the double imaging assembly 1910 may be attached to a movable imaging cart 1900 comprising a base section 1903 having wheels 1901 for rolling the imaging cart 1900 over a surface such as a floor. A vertical column 1907 is attached to the base 1903. An extendable horizontal arm 1909 is movably attached to the column 1907 to allow raising and lowering of the horizontal arm, relative to the vertical column 1907, and thereby raising and lowering the double imaging assembly 1910 together therewith. The horizontal arm 1909 may be extendable and retractable in a horizontal direction away from and toward the vertical column 1907, such as being fabricated in a telescoping configuration. The horizontal arm 1909 may be attached to the double imaging assembly 1910 via a joint 2407 that is rotatable in at least two dimensions, and preferably in three dimensions as described herein below. The imaging cart 1900 may be outfitted with a bin 2405 for storing a detector 2404 therein, which bin may also be configured with an electrical connector to engage an electrical connector of the detector 2404 for charging the detector 2404. A handle 2403 attached to the vertical column 1907 near the top thereof, allows manual control over rolling movement of the imaging cart 1900 using the wheels 1901. A pedal 2406 may be provided for locking the wheels 1901 to prevent free rolling of the wheels 1901.

Figure 24A:
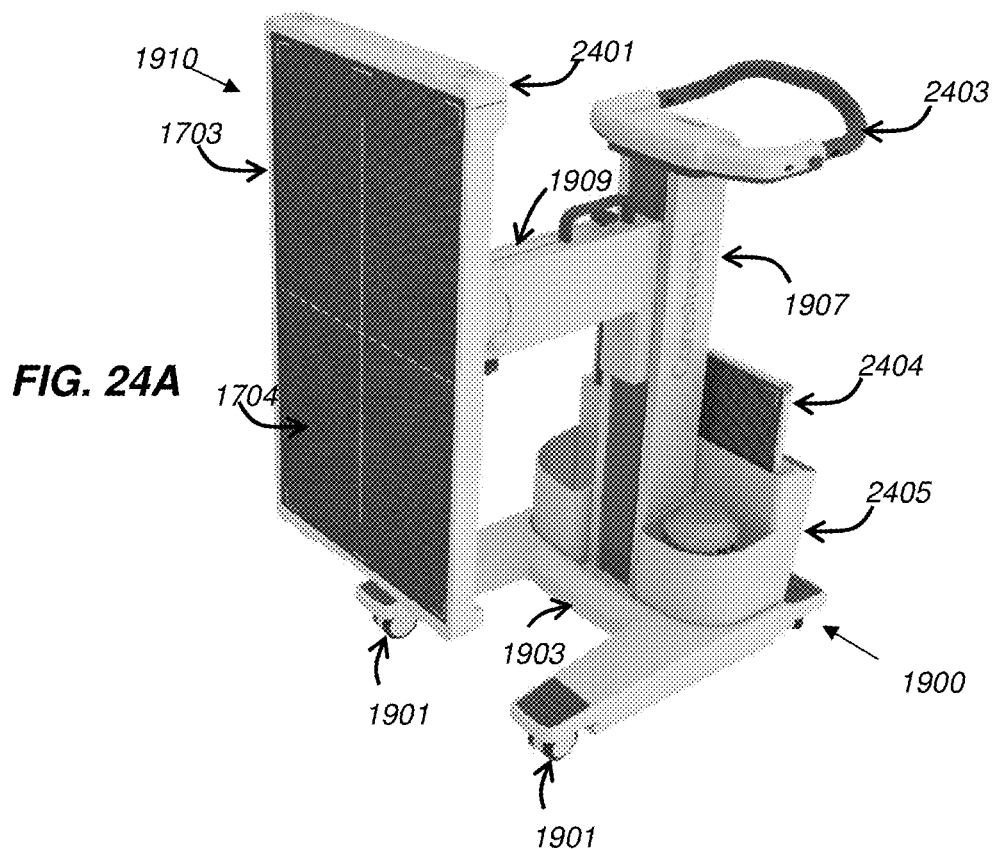
FIGS. 24A-F illustrate various positions of an exemplary DR LLI mobile system.
Figure 24B:
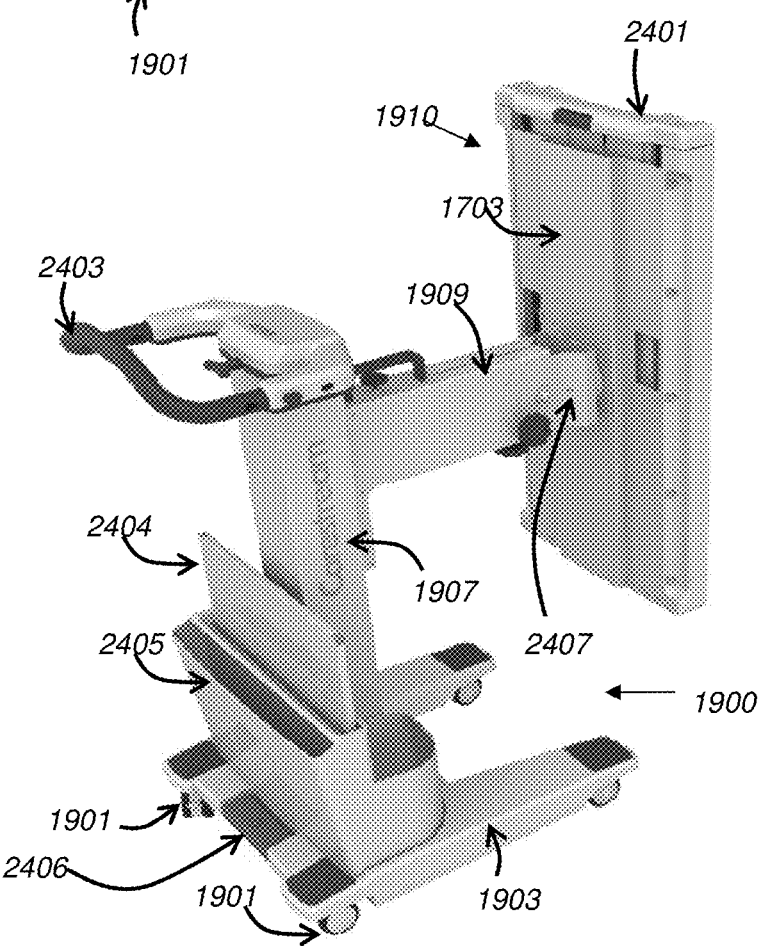
Figure 24C:
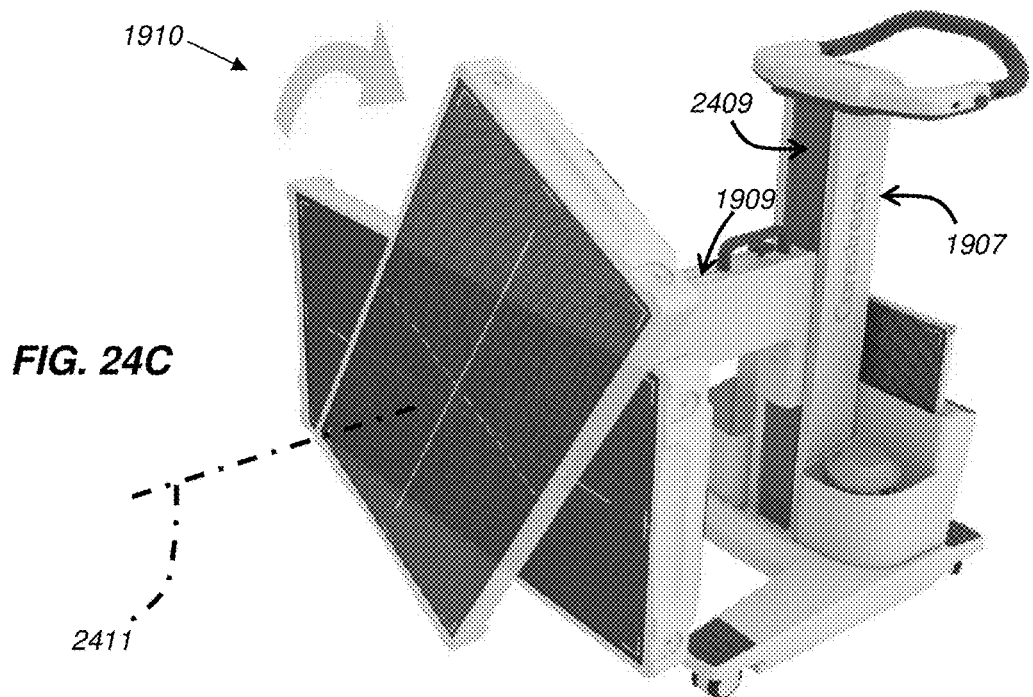
Figure 24D:
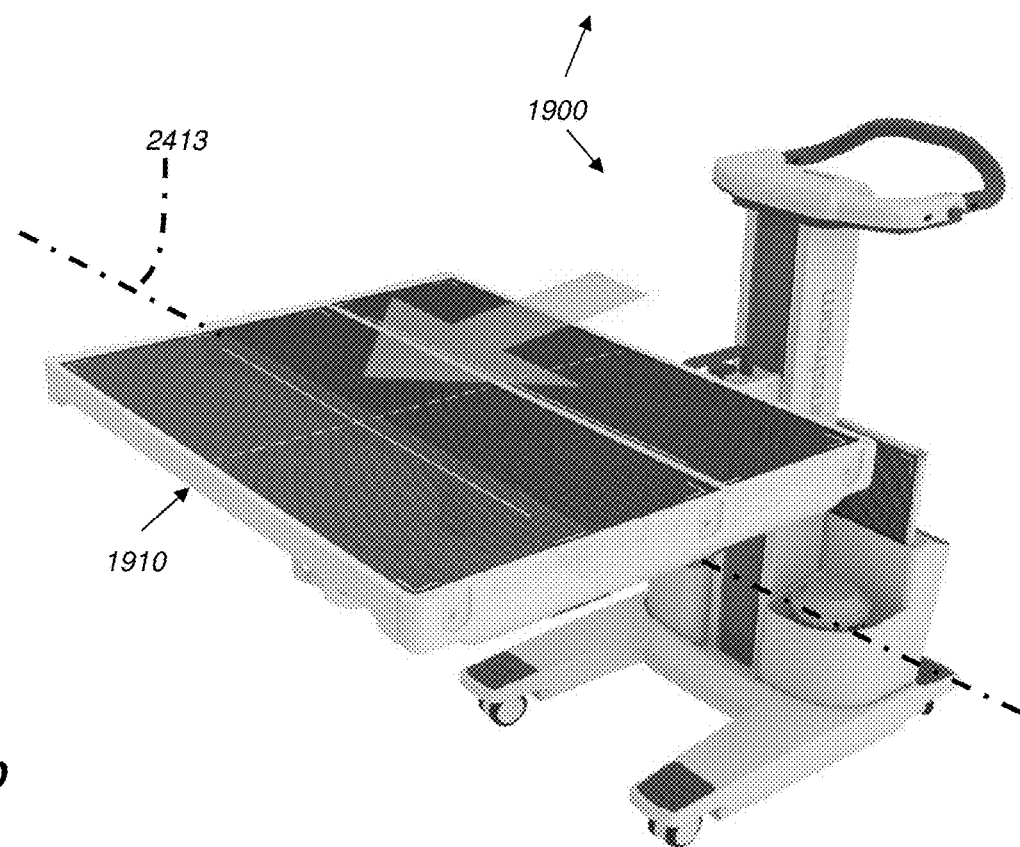

FIG. 24C illustrates movement of the horizontal arm 1909 downward along a track 2409 in the vertical column 1907, as compared with FIG. 24A, and a rotation of the double imaging assembly 1910 about a first horizontal axis 2411 intersecting, and perpendicular to, the vertical arm 1907. FIG. 24D illustrates movement (rotation) of the double imaging assembly 1910 about a second horizontal axis 2413 that is generally perpendicular to the first horizontal axis 2411 to enable imaging of a supine patient by positioning the double imaging assembly 1910 beneath the patient. The positioning of imaging assembly 1910 as described herein above and illustrated in FIGS. 24A-D enables erect, supine, and cross-table imaging of a patient in an x-ray exam room or in bedside locations such as a patient room, operating room, emergency room or intensive care unit. FIG. 24D also illustrates movement of the double imaging assembly 1910 horizontally (arrow) by extending the telescoping horizontal arm 1909 away from the vertical column 1907. In one embodiment, the vertical column 1907 may also be fabricated in a telescoping configuration to raise and lower the double imaging assembly 1910.

Figure 24E:
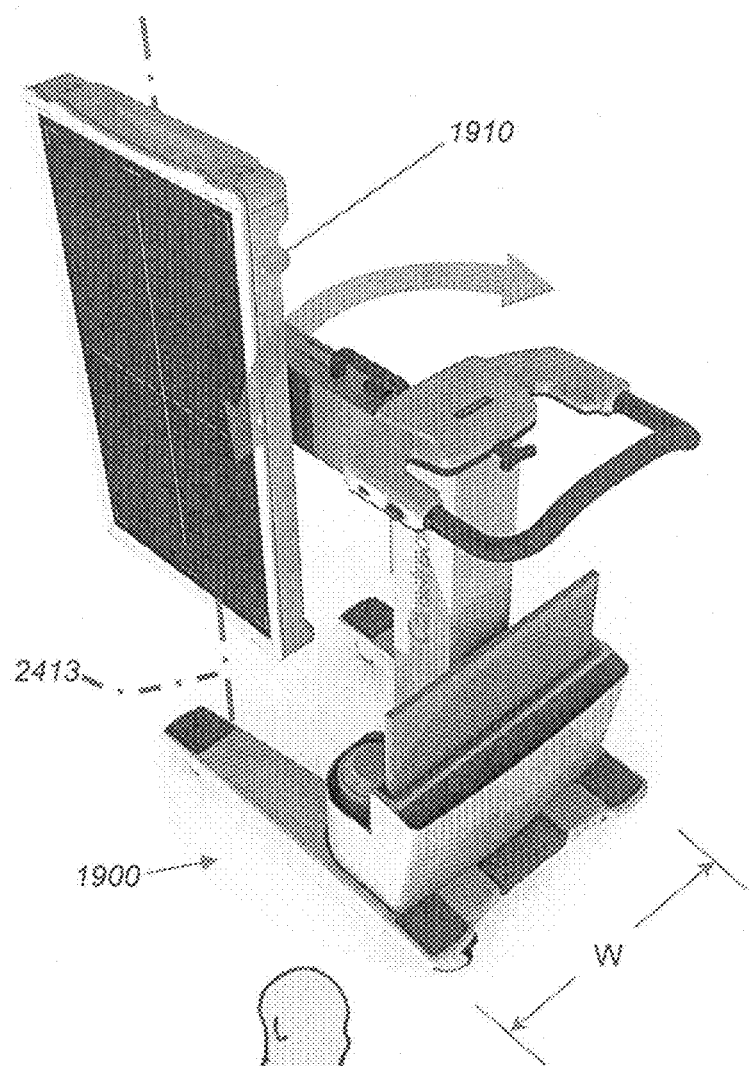
Figure 24F:
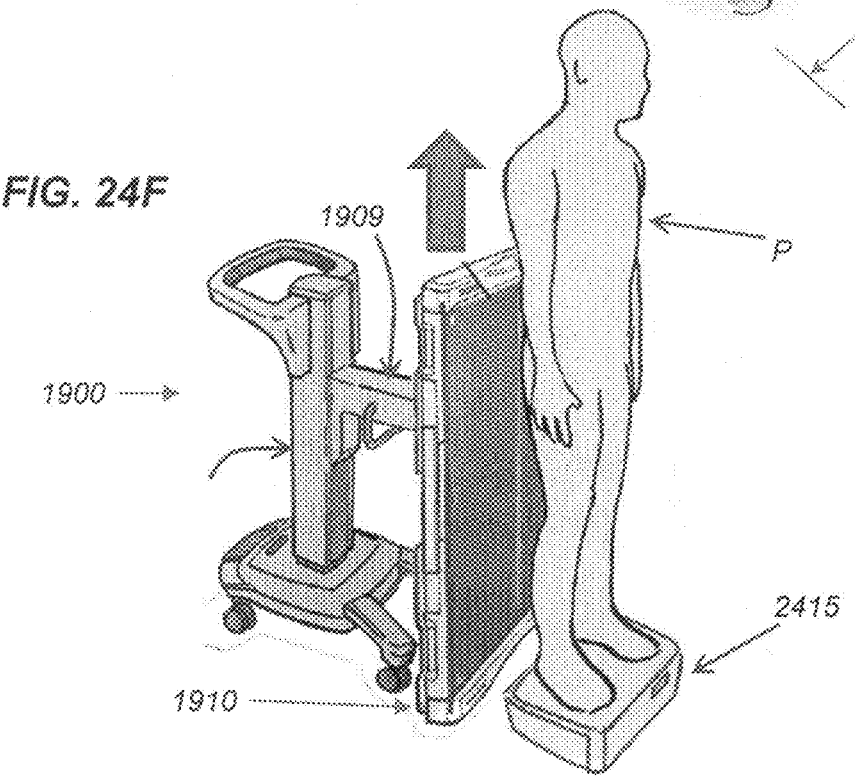

FIG. 24E illustrates movement of the double imaging assembly 1910 about a third axis 2413 that is vertically oriented and is perpendicular to both horizontal axes 2411 and 2413. The orientation of the double imaging assembly 1910 as illustrated in FIG. 24E allows positioning the double imaging assembly 1910 closer to an obstacle, such as parallel to a wall in an imaging room, because the width dimension W of the imaging cart 1900 is less than the perpendicular length dimension thereof. FIG. 24F illustrates lowering of the double imaging assembly 1910 by lowering the horizontal arm 1909 to enable capturing a long length lower body (e.g., legs) DR image of a patient P standing on a short pedestal 2415. The horizontal arm 1909 may also be moved vertically upward along vertical column 1907 to enable capturing a long length upper body (e.g., spine) DR image of a patient P. In one embodiment of the imaging assembly 1910, the imaging area of the two detectors may be about 17"×33" and the imaging area of the three detector embodiment may be about 17"×49", although these dimensions may vary based at least on sizes of the individual detectors and on the imaging assembly overlap dimensions.

Figure 25A:
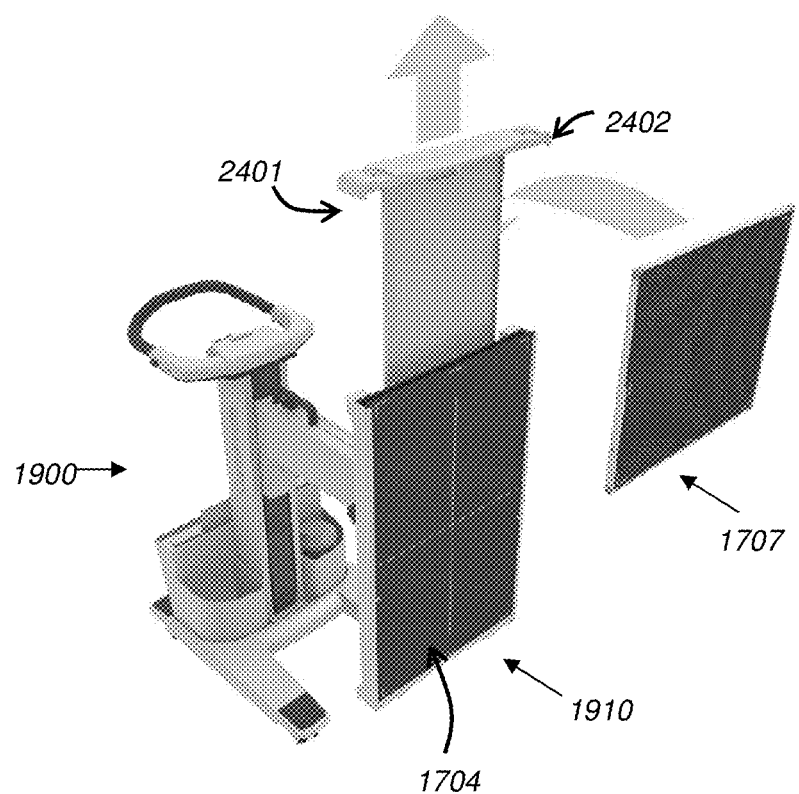
FIGS. 25A-B demonstrate a conversion of an exemplary DR LLI mobile system.
Figure 25B:
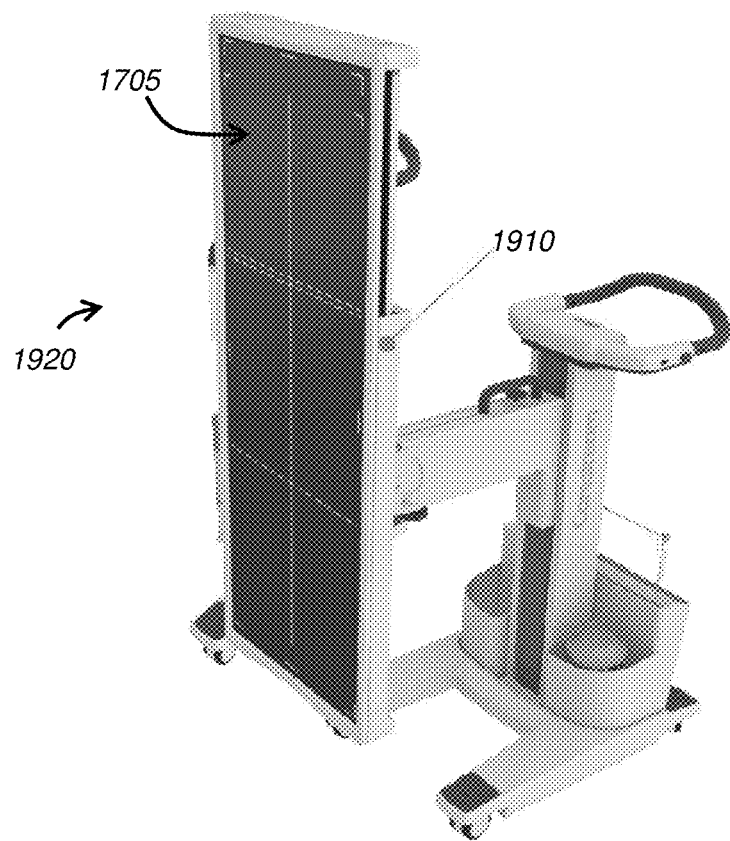

FIGS. 25A-B are perspective views illustrating conversion of the double imaging assembly 1910 into the triple imaging assembly 1920. As illustrated in FIG. 25A, the extendible top 2401 may be extended to allow insertion of detector 1707 under a lip 2402 of the extendible top 2401. The third detector 1707 is positioned against a top edge of the housing 1703 (not visible) behind double sized grid 1704 of the double imaging assembly 1910, as explained above in relation to FIGS. 23A-D. This electro-mechanical engagement of the third detector 1707 to the two-detector housing 1703 is also described above in relation to FIGS. 21A-B and FIGS. 22A-D. After the third detector 1707 is inserted and positioned against the top of the housing 1703 within double imaging assembly 1910, a lip 2402 of the extendible top 2401 may be positioned against the top edge of third detector 1707 to secure it in position parallel to the two detectors 1701, 1702 of the double imaging assembly 1910. As illustrated in the perspective view of FIG. 25B, a triple sized grid 1705 is used to replace the double sized grid 1704, thereby completing the assembly of triple imaging assembly 1920, which is maneuverable in three dimensions similar to the movement of the double imaging assembly 1910 described above in relation to FIGS. 24A-F.

Figure 26A:
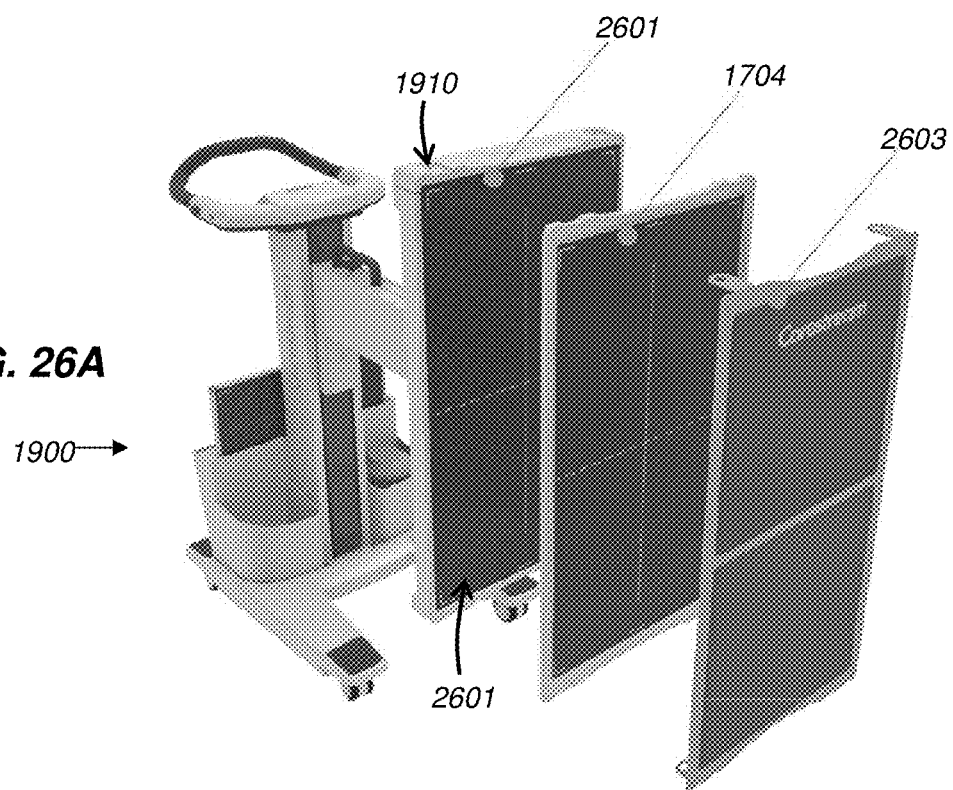
FIGS. 26A-B illustrate further features of an exemplary DR LLI mobile system.
Figure 26B:
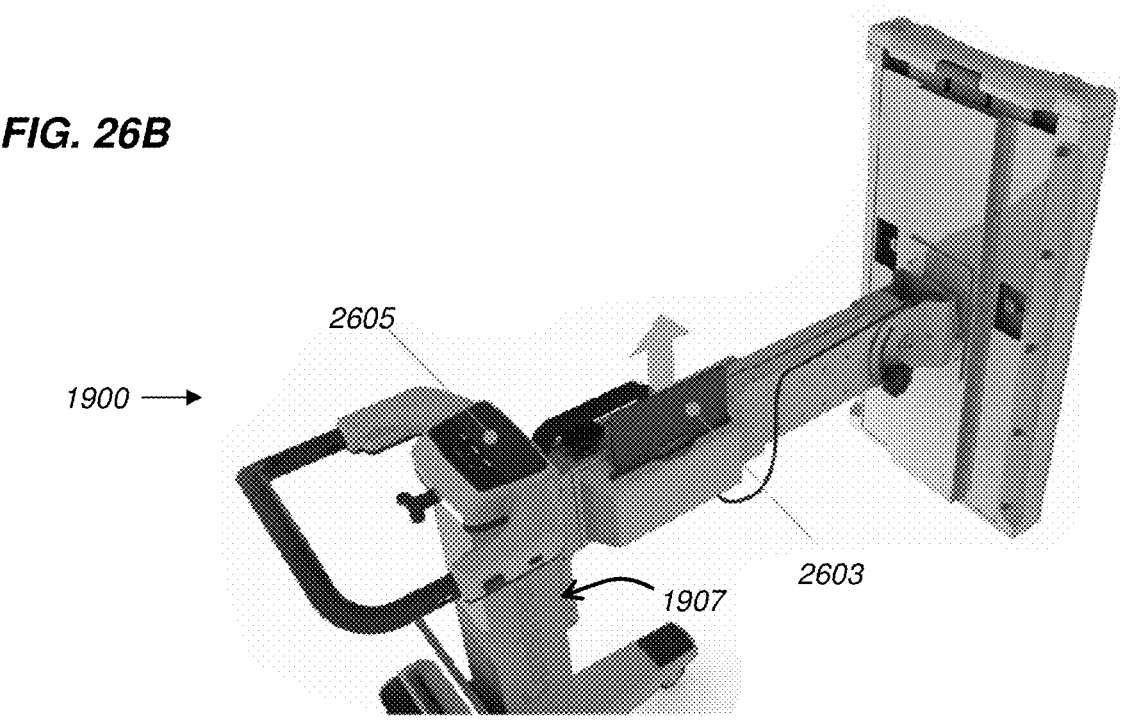

FIGS. 26A-B illustrate features of the movable imaging cart 1900 whereby the double imaging assembly 1910 comprises a radiolucent front surface 2601 and the double sized grid 1704, which double sized grid 1704 may be attached to the double imaging assembly 1910 in front of the radiolucent front surface 2601. A soft cover 2603 may also be positioned over the double sized grid 1704 to protect the double imaging assembly 1910 while being transported using the movable imaging cart 1900. FIG. 26B illustrates a bin attached to the horizontal arm 1909 to hold a detector, battery, or other device 2603. An LED monitor 2605 may be placed on a top of the vertical column 1907 to display various status of the imaging cart 1900.

Figure 27A:
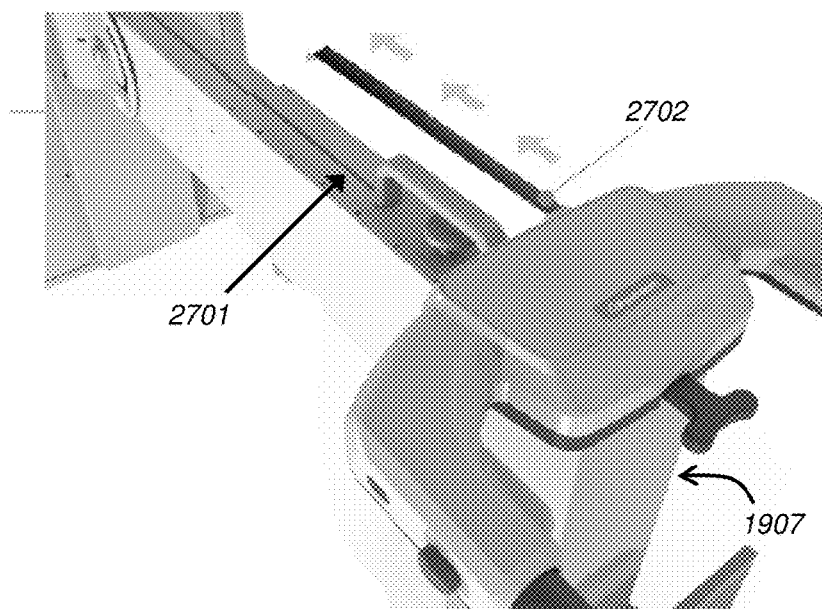
FIGS. 27A-B illustrate further features of an exemplary DR LLI mobile system.
Figure 27B:
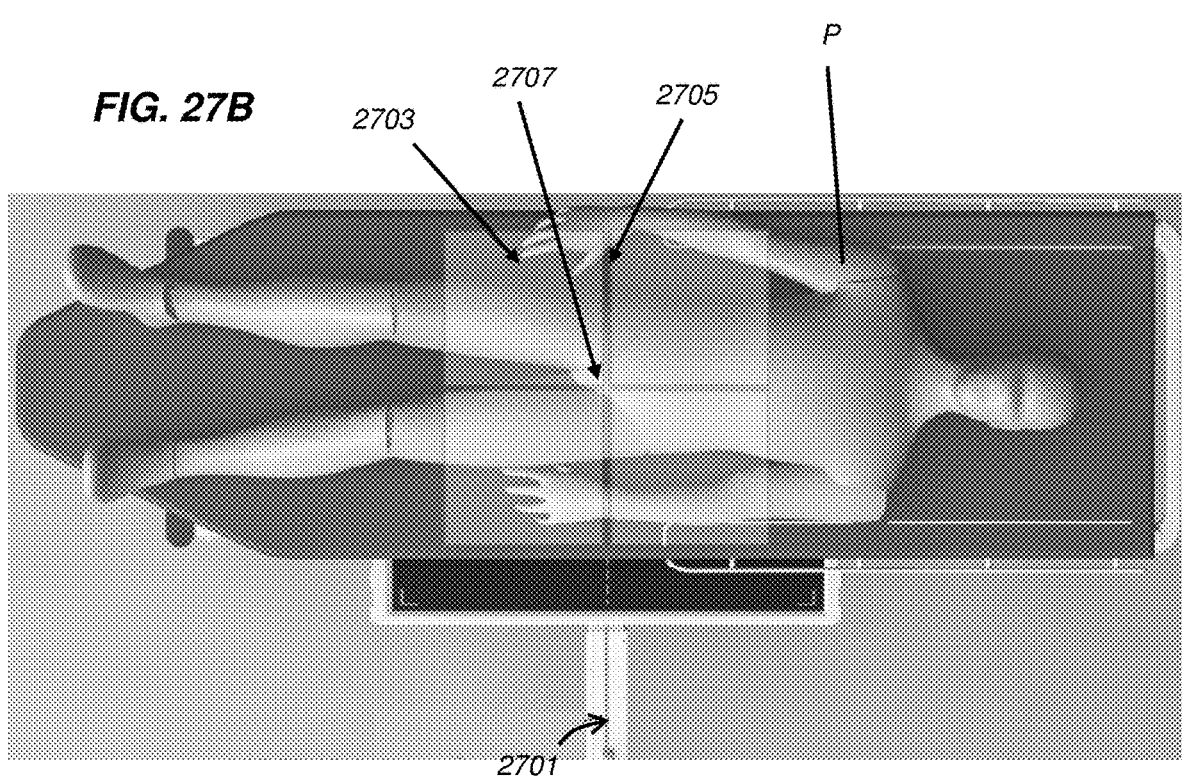

FIGS. 27A-B illustrate features of the imaging cart 1900 to enable precise placement of the imaging assembly 1910, 1920, during radiographic image capture. FIG. 27A illustrates a centerline marking 2701 aligned on fixed and telescoping portions of the horizontal arm 1909 which may be used together with illuminated collimator crosshairs 2705 emitted by an x-ray tube head and projected onto a patient P being radiographically imaged. As shown in FIG. 27B, the centerline 2701 on the horizontal arm 1909 may be visually aligned by a technician with a crosshair 2705 projected onto a collimator illumination region 2703. To align a center 2707 of the projected crosshairs 2705 with a center of the imaging assembly 1910, 1920, an extendable coiled tape measure 2702 may be provided near a top of the vertical column 1907 to measure and record a distance to a center of the imaging assembly 1910, 1920. The tape measure may then be manually extended over the patient P until the recorded distance on the tape measure 2702 aligns with a center 2707 of the illuminated collimator cross hairs 2705.

Figure 28A:
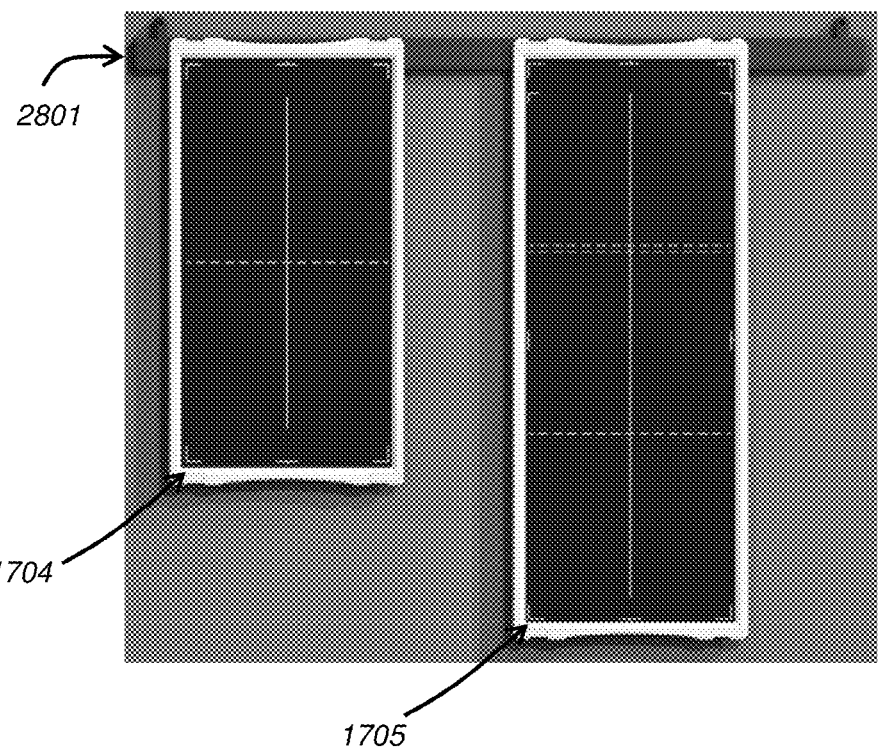
FIGS. 28A-B illustrate further features of an exemplary DR LLI mobile system.
Figure 28B:
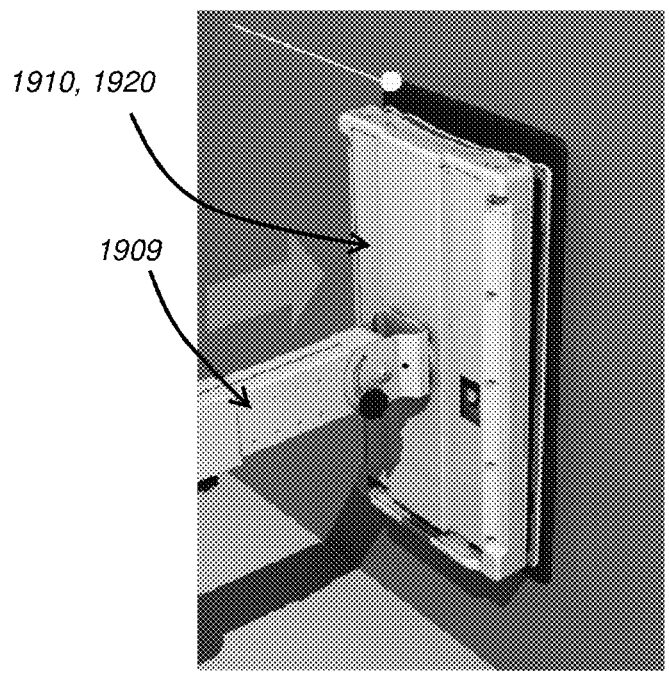

FIGS. 28A-B illustrate use of a bracket 2801 secured to a wall for hanging and storing the double and/or triple sized grids 1704, 1705. As shown in FIG. 28B, the movable imaging cart 1900 may be wheeled up to the hanging grid to position the imaging assembly 1910 or 1920 near to, or in contact with, the hanging grid 1704, 1705, in order to more easily place one of the double and/or triple sized grids 1704, 1705 onto a front of the imaging assembly 1910, 1920, respectively. Similarly, the movable imaging cart 1900 may be wheeled up to the bracket 2801 to position the imaging assembly 1910 or 1920 near the bracket 2801 in order to more easily remove one of the double and/or triple sized grids 1704, 1705, from the front of the imaging assembly 1910, 1920, respectively, to hang it on the bracket 2801.

Figure 29A:
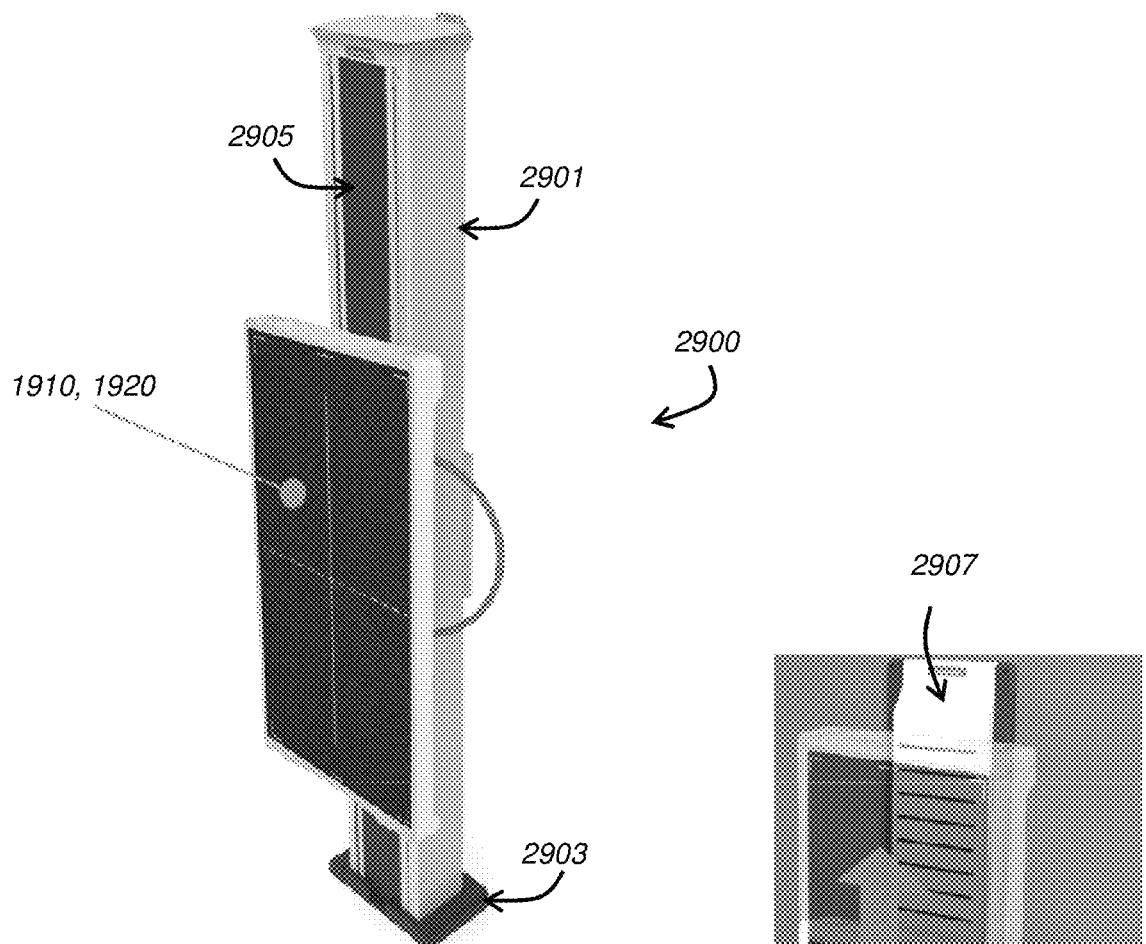
FIGS. 29A-B illustrate an exemplary floor mounted and wall mounted DR LLI system, respectively.
Figure 29B:
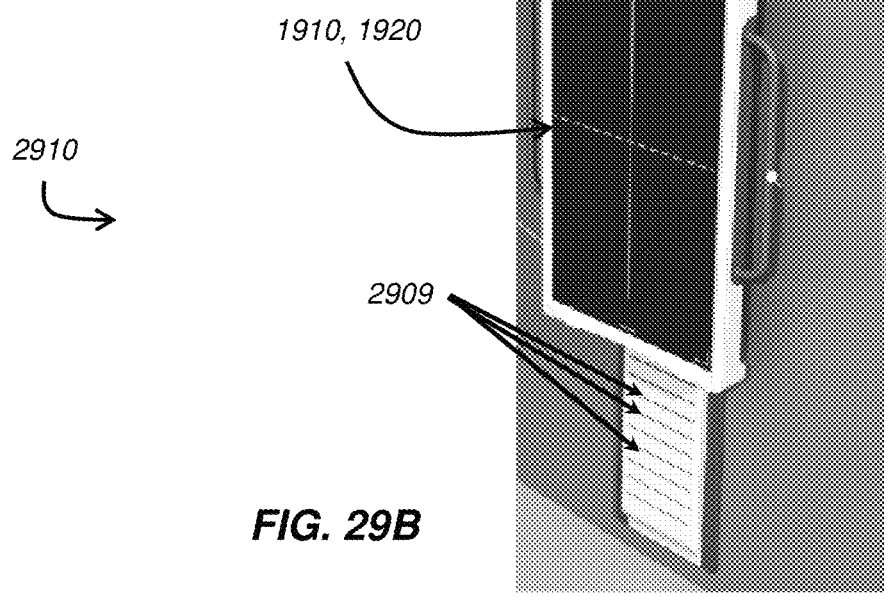

FIGS. 29A-B are perspective views of embodiments of immobile imaging systems 2900, 2910, respectively, whereby imaging assemblies 1910, 1920 (embodiment using only imaging assembly 1910 is illustrated in FIGS. 29A-B) may be movably attached to immobile structures. FIG. 29A illustrates a floor mounted embodiment 2900 whereby a vertical column 2901 may be secured by its base 2903 to a floor in an imaging facility. As described herein with respect to vertical column 1907 of the movable cart 1900, the floor mounted column 2901 includes a vertical track 2905 whereby the imaging assembly 1910, 1920, attached thereto, may be moved vertically along the track 2905 of the vertical column 2901 to a desired height for imaging a patient positioned proximate the imaging assembly 1910, 1920.

FIG. 29B illustrates a wall mounted embodiment having a vertical slotted panel 2907 that may be secured to a wall in an imaging facility. The wall mounted panel 2907 includes a number of slots 2909 in the vertical panel 2907 whereby the imaging assembly 1910, 1920, may be moved vertically along the panel 2907 to a desired height for imaging a patient positioned proximate the imaging assembly 1910, 1920. The slots 2909 may serve to engage a detent mechanism of the imaging assembly 1910, 1920. The imaging assembly 1910, 1920 may include a detent mechanism attached to a rear side thereof to selectively engage one of the slots 2909 of the vertical panel 2905 at a desired height to secure the imaging assembly 1910, 1920, at the desired height. In the embodiments described herein: the movable cart 1900, the floor mounted embodiment 2900, and the wall mounted embodiment 2910, the imaging panel assembly 1910, 1920, may be lowered such that a bottom edge of the imaging panel assembly 1910, 1920, approaches a floor to within an inch thereof, or may be lowered to make contact with the floor.

Figure 30:
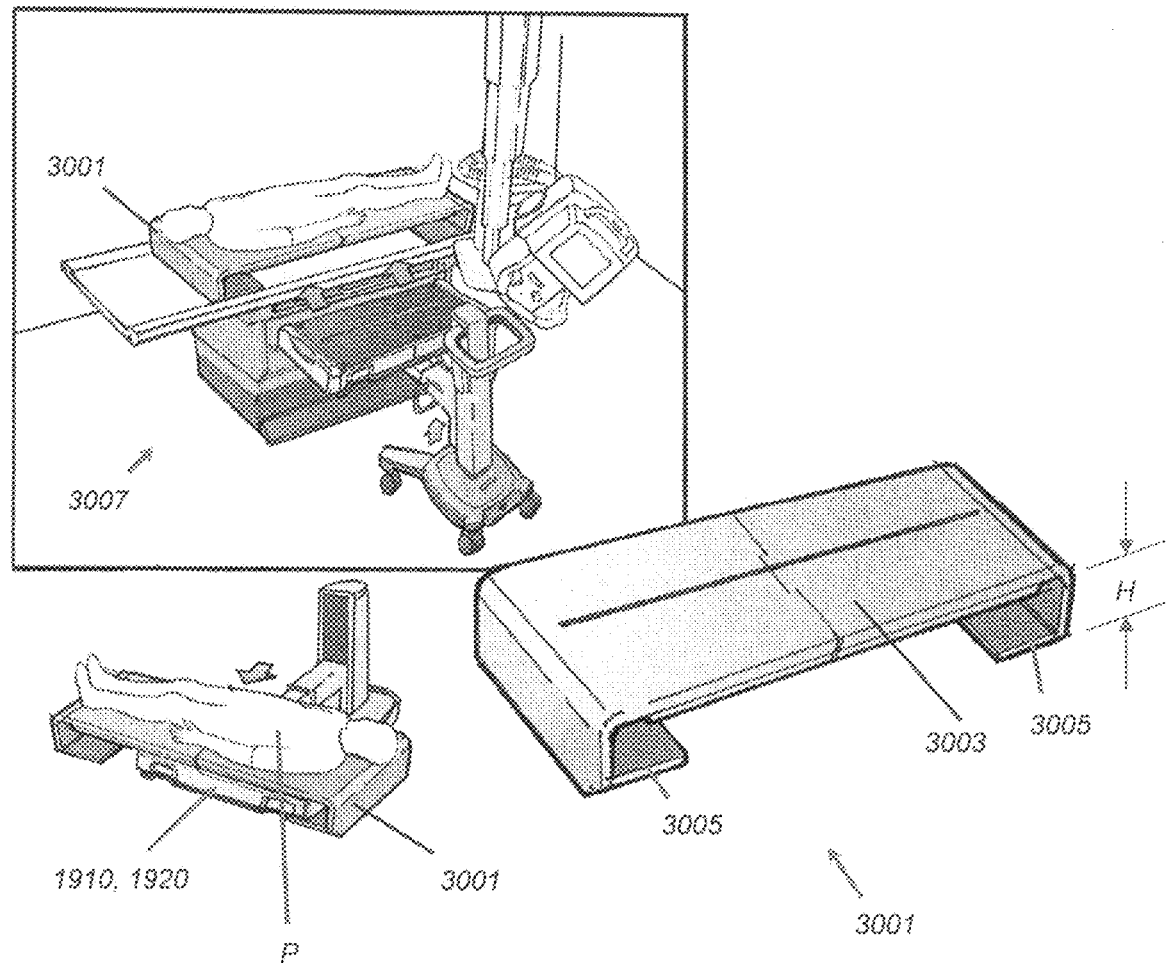
FIG. 30 illustrates a supine patient table.

FIG. 30 illustrates a radiolucent patient table 3001 that may be used together with the movable imaging cart 1900 described herein. The patient table 3001 comprises an upper surface 3003 for supporting a supine patient P. The patient table 3001 further comprises supports 3005 at opposite edges of the table 3001 to provide a height H beneath the upper surface 3003 sufficient for positioning an imaging assembly 1910, 1920 underneath the support surface 3003. In other embodiments, the supports may be formed as table legs, wheels for rolling the patient table across a floor, beams, or other support shapes. The patient table 3001 may be positioned on existing imaging equipment in an x-ray exam room such as an existing x-ray table 3007, or the patient table 3001 may be positioned on a floor of the x-ray exam room in order to maximize a SID as between an x-ray tube and an imaging assembly 1910, 1920, positioned underneath the patient table 3001. In some circumstances, the x-ray tube in an exam room may not be maneuverable to a sufficient height for maximum LLI exposure, therefore, lowering a supine patient as close as possible to a floor using the patient table 3001 may be advantageous. In either position, i.e., on an existing x-ray table or on a floor, the movable imaging cart 1900 is capable of adjusting a height of the imaging assembly 1910, 1920, by vertically moving the horizontal arm 1909 to an appropriate height and then wheeling the mobile imaging system 1900 or extending the telescoping horizontal arm 1909 to position the imaging assembly underneath the imaging table 3001.

As will be appreciated by one skilled in the art, aspects of the present invention may be embodied as a system, an apparatus, and a method, for capturing long length images of a subject using multiple DR detectors. This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A digital radiographic detector system comprising:
   a plurality of DR detectors each comprising a radiographic imaging array;
   a base having a plurality of wheels for wheeling the system over a surface;
   a vertical column attached to the base;
   an arm having a distal end and a proximal end opposite the distal end, the proximal end of the arm attached to the vertical column, the arm configured to move vertically along the vertical column; and
   a housing attached to a distal end of the arm, the housing comprising a major surface made from a radiolucent material;
   wherein the housing encloses and supports therewithin the plurality of DR detectors, and wherein the radiographic imaging array of the plurality of DR detectors each faces the housing major surface made from the radiolucent material.

2. The system of claim 1, further comprising:
   a rotatable joint attached to the housing and to the arm to rotatably attach the housing to the arm, the rotatable joint configured to enable variable positioning of the housing into at least two positions, wherein a first position of the housing includes the major housing surface positioned in a vertical plane facing away from the column, and wherein a second position includes the major housing surface lying in a horizontal plane facing upward.

3. The system of claim 1, wherein the housing supports therewithin the plurality of DR detectors each in a plane parallel to one another, wherein the housing is configured to receive an additional DR detector and to secure the additional DR detector within the housing in a plane parallel to the planes of the plurality of DR detectors.

4. The system of claim 1, further comprising a wall hanger for hanging a grid thereon, the wall hanger configured to facilitate securing the hanging grid onto the DR imaging system when the DR imaging system is wheeled close to the wall hanger such that the housing contacts the hanging grid.

5. The system of claim 1, wherein at least one of the plurality of detectors comprises a first communication connector configured to receive and engage a corresponding second communication connector on an additional detector, and wherein the additional DR detector is configured to communicate detector identification information through the communicatively engaged first and second connectors.

6. The system of claim 5, wherein the plurality of detectors and the additional detector each comprise electronic wireless communication circuits, and wherein the additional DR detector is configured to communicate detector identification information wirelessly or through the communicatively engaged first and second connectors.

7. The system of claim 6, wherein the plurality of detectors and the additional detector are configured to communicate with only one controller external to the DR detector system, and wherein the one controller is configured to control power distribution to the detectors within the housing and to control data connections between the controller and the detectors within the housing.

8. The system of claim 1, further comprising:
   a rotatable joint attached to the housing and to the arm to rotatably attach the housing to the arm, the rotatable joint configured to enable variable positioning of the housing into at least two positions, wherein a first position of the housing includes the major housing surface positioned in a vertical plane facing in a horizontal first direction, and wherein a second position includes the major housing surface revolved about an axis parallel to the column facing in a horizontal second direction perpendicular to the first direction.

9. The system of claim 1, further including a single external connector on the housing that includes channels for transmitting power to the detectors, data to and from the detectors, and control instructions to and from the plurality of DR detectors.

10. A digital radiographic detector system comprising:
    a plurality of DR detectors each comprising a radiographic imaging array;
    a base affixed to a floor;
    a vertical column attached to the base;
    a movable support attached to the vertical column, the support configured to move vertically along the vertical column; and
    a housing attached to the vertical support, the housing comprising a major surface made from a radiolucent material,
    wherein the housing encloses and supports therewithin the plurality of DR detectors, and wherein the radiographic imaging array of the plurality of DR detectors each faces the major housing surface.

11. The system of claim 10, further comprising:
a rotatable joint attached to the housing and to the movable support to rotatably attach the housing to the support, the rotatable joint configured to enable variable positioning of the housing into at least two positions, wherein a first position of the housing includes the major housing surface positioned in a vertical plane facing away from the column, and wherein a second position includes the major housing surface rotated in the vertical plane.

12. The system of claim 10, wherein the housing supports therewithin the plurality of DR detectors each in a plane parallel to one another, wherein the housing is configured to receive an additional DR detector and to secure the additional DR detector within the housing in a plane parallel to the planes of the plurality of DR detectors.

13. The system of claim 10, wherein the housing is configured to secure thereto a grid in a position parallel to the major surface of the housing.

14. The system of claim 10, wherein at least one of the plurality of detectors comprises a first communication connector configured to receive and engage a corresponding second communication connector on an additional DR detector, and wherein the additional DR detector is configured to communicate detector identification information through the communicatively engaged first and second connectors.

15. The system of claim 10, wherein the plurality of detectors and the additional detector each comprise electronic wireless communication circuits, and wherein the additional DR detector is configured to communicate detector identification information wirelessly or through the communicatively engaged first and second connectors.

16. The system of claim 15, wherein the plurality of detectors and the additional detector are configured to communicate with only one controller external to the DR detector system, and wherein the one controller is configured to control power distribution to the detectors within the housing and to control data connections between the controller and the detectors within the housing.

17. The system of claim 10, further including a single external connector on the housing that includes channels for transmitting power to the detectors, data to and from the detectors, and control instructions to and from the plurality of DR detectors.

18. A digital radiographic detector system comprising:
a plurality of DR detectors each comprising a radiographic imaging array;
a vertical hanger having a plurality of first detent portions arranged vertically in relation to one another, the vertical hanger attached to a vertical surface;
a manually movable support attached to the vertical hanger, the support configured to move vertically along the vertical hanger and comprising a second detent portion to lockably engage the movable support to any one of the first detent portions; and
a housing attached to the movable support, the housing comprising a major surface made from a radiolucent material, which major surface faces away from the vertical surface,
wherein the housing encloses and supports therewithin the plurality of DR detectors, and wherein the radiographic imaging array of the plurality of DR detectors each faces the major housing surface.

19. The system of claim 18, further comprising:
a rotatable joint attached to the housing and to the movable support, the rotatable joint configured to enable variable positioning of the housing into at least two positions, wherein a first position of the housing includes the major housing surface positioned in a vertical plane facing away from the vertical surface, and wherein a second position includes the major housing surface rotated in the vertical plane.

20. The system of claim 19, wherein the housing supports therewithin the plurality of DR detectors each in a plane parallel to one another, wherein the housing is configured to receive an additional DR detector and to secure the additional DR detector within the housing in a plane parallel to the planes of the plurality of DR detectors.

* * * * *